US007351690B2

(12) United States Patent
Sharma et al.

(10) Patent No.: US 7,351,690 B2
(45) **Date of Patent: *Apr. 1, 2008**

(54) KNOCKOUT IDENTIFICATION OF TARGET-SPECIFIC SITES IN PEPTIDES

(75) Inventors: Shubh D. Sharma, Cranbury, NJ (US); Yi-Qun Shi, East Brunswick, NJ (US); Margarita Bastos, Plainsboro, NJ (US); Ramesh Rajpurohit, Hillsboro, NJ (US); Hui-Zhi Cai, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/769,695

(22) Filed: Jan. 30, 2004

(65) Prior Publication Data

US 2004/0248212 A1 Dec. 9, 2004

Related U.S. Application Data

(63) Continuation-in-part of application No. 10/464,117, filed on Jun. 17, 2003, which is a continuation of application No. PCT/US01/50075, filed on Dec. 19, 2001.

(60) Provisional application No. 60/256,842, filed on Dec. 19, 2000, provisional application No. 60/304,835, filed on Jul. 11, 2001, provisional application No. 60/327,835, filed on Oct. 4, 2001, provisional application No. 60/444,129, filed on Jan. 31, 2003.

(51) Int. Cl.
*A61K 38/16* (2006.01)

(52) U.S. Cl. .......................... 514/6; 530/300; 530/326; 530/327; 530/328; 530/329; 530/330; 530/331; 435/7.1

(58) Field of Classification Search ................. 435/7.1; 530/300, 326, 327, 328, 329, 330, 331; 424/1.69; 514/6

See application file for complete search history.

(56) References Cited

U.S. PATENT DOCUMENTS

| | | | |
|---|---|---|---|
| 5,834,250 | A | 11/1998 | Wells et al. |
| 5,891,418 | A | 4/1999 | Sharma |
| 6,027,711 | A | 2/2000 | Sharma |
| 6,083,758 | A | 7/2000 | Imperiali et al. |
| 6,084,066 | A | 7/2000 | Evans et al. |
| 6,278,794 | B1 | 8/2001 | Parekh et al. |
| 6,331,285 | B1 | 12/2001 | Sharma |
| 2001/0000807 | A1 | 5/2001 | Freire et al. |

FOREIGN PATENT DOCUMENTS

| | | |
|---|---|---|
| WO | WO 96/40293 | 12/1996 |
| WO | WO 00/23564 | 4/2000 |
| WO | WO 00/36136 | 6/2000 |
| WO | WO 00/57309 | 9/2000 |
| WO | WO 01/35316 | 5/2001 |
| WO | WO 01/50355 | 7/2001 |
| WO | WO 01/59066 | 8/2001 |
| WO | WO 02/064734 | 8/2002 |

OTHER PUBLICATIONS

Chan, W. Y., et al., "Discovery and Design of Novel and Selective Vasopressin and Oxytocin Agonists and Antagonists: The Role of Bioassays", *Experimental Physiology, vol. 85 Suppplement 1*, Abstract only supplied,(Mar. 2000),7S-18S.

Deschodt-Lanckman, Monique, et al., "In Vitro Action of Bombesin and Bombesin-Like Peptides on Amylase Secretion, Calcium Efflux, and Adenylate Cyclase Activity in Rat Pancreas", *Journal of Clinical Investigation* vol. 58, (Oct. 1976), 891-898.

Grant, Gregory A., "Synthetic Peptides. A User's Guide", *W.H. Freeman and Co.*, New York 1992, 11-14.

Hampton, Lori L., et al., "Loss of Bombesin-Induced Feeding Suppression in Gastrin-Releasing Peptide receptor-Deficient Mice", *Proc. Natl. Acad. Sci. USA*, vol. 95, (Mar. 1998),3188-3192.

Hruby, V J., "Emerging Approaches in the Molecular Design of Receptor-Selective Peptide Ligands: Conformational, Topographical and Dynamic Considerations", *Biochemical Journal*, (1990) 268, 249-262.

Leban, Johann J., et al., "Development of Potent Gastrin-Releasing Peptide Antagonists Having a D-Pro-PSI(CH2NH)-Phe-NH2 C Terminus", *Proc. Natl. Acad. Sci. USA*, vol. 90, (Mar. 1993),1922-1926.

Maccoll, R. , "Interrelationships among biological active, disulfide bonds, second structure, and themetal binding of a chemically synthesized 34-aminio acid peptide derived from alpha-fetoprotein", *Biochimica Et Biophysic ACTA-General Subjects*; vol. 1528, No. 2-3, (Oct. 3, 2001), 127-134.

Moody, Terry W., et al., "Bombesin: Specific Binding to Rat Brain Membranes", *Proc. Natl. Acad. Sci. USA*, vol. 75, No. 11, (Nov. 1978),5372-5376.

Simmonds, R. G., et al., "Synthesis of Disulfide-Bridged Fragments of Omega-Conotoxins GVIA and MVIIA. Use of Npys as a Protecting/Activating Group for Cysteine in Fmoc Syntheses", *Int J Pept Protein Res.* vol.43(4), Abstract only supplied,(Apr. 1994),363-366.

(Continued)

*Primary Examiner*—Chih-Min Kam
(74) *Attorney, Agent, or Firm*—Stephan A. Slusher

(57) ABSTRACT

The invention provides methods for identification and determination of target-specific sites in peptides and proteins, including a method for determining the primary sequence of a secondary structure within a known parent polypeptide that binds to the target of interest. In one embodiment of the invention, a residue or mimetic containing a nitrogen atom and a sulfur atom available for binding to a metal ion is serially substituted for single residues in or inserted between adjacent residues in a known primary sequence of a peptide or protein. The resulting sequence is complexed with a metal ion thereby forming a metallopeptide. The resulting metallopeptides are then used in binding or functional assays related to the target of interest, and the metallopeptide(s) which result in significant or substantially decreased or changed binding or functionality are determined to identify the primary sequence involved in such binding or functionality.

26 Claims, 3 Drawing Sheets

OTHER PUBLICATIONS

Soto, Claudio, ""beta"-Sheet Breaker Peptides Inhibit Fobrillogenesis in a Rat Brain Model of Amyloidosis of Amyloidosis: Implications for Alzheimer's Therapy", *Nature Medicine*; vol. 4, No. 7, (Jul. 1998),822-826.

Soto, Claudio, "Alzheimer's and Prion Diseases as Disorders of Protein Conformation: Implications for the Design of Novel Therapeutic Approaches", *J Mol Med* vol. 77, (1999),412-418.

Soto, Claudio , "Plaque Busters: Strategies to Inhibit Amyloid Formation in Alzheimer's Disease", *Molecular Medicine Today*, vol. 5, (Aug. 1999),343-350.

Soto, Clauadio, "Reversion of Prion Protein Conformational Changes by Synthetic", *The Lancet*, vol. 355, (Jan. 5, 2000),192-197.

Toniolo, C. , "Conformationally Restricted Peptides Through Short-Range Cyclizations", *Int J Peptide Protein Res* vol. 35, (1990),287-300.

Yamada, Kazuyuki , et al., "Bombesin-Like Peptides: Studies on Food Intake and Social Behaviour with Receptor Knock-Out Mice", *The Finnish Medical Society Duodecim*, vol. 32, (Ann. Med 2000),519-529.

KNOCKOUT IDENTIFICATION OF TARGET-SPECIFIC SITES IN PEPTIDES

This application is a continuation-in-part application of U.S. patent application Ser. No. 10/464,117, entitled Identification of Target-Specific Folding Sites in Peptides and Proteins, filed on Jun. 17, 2003, which claims the benefit of the filing of PCT/US01/50075, entitled Identification of Target-Specific Folding Sites in Peptides and Proteins, filed on Dec. 19, 2001; U.S. Provisional Patent Application Ser. No. 60/256,842, entitled Iterative Deconvolution Of Target-Specific Folding Sites In Peptides, filed on Dec. 19, 2000; of U.S. Provisional Patent Application Ser. No. 60/304,835, entitled Metallopeptides for Treatment of Alzheimer's and Prion Disease, filed on Jul. 11, 2001; and of U.S. Provisional Patent Application Ser. No. 60/327,835, entitled Urokinase-Type Plasminogen Activator Receptor Specific Metallopeptides, filed on Oct. 4, 2001; and the specification thereof of each is incorporated herein by reference.

This application claims the benefit of the filing of U.S. Provisional Patent Application Ser. No. 60/444,129, entitled Knockout Identification Of Target-Specific Sites In Peptides, filed on Jan. 31, 2003, and the specification thereof is incorporated herein by reference.

BACKGROUND OF THE INVENTION

1. Field of the Invention (Technical Field)

The present invention relates to methods for identification and determination of target-specific sequences within peptides and proteins; methods to determine the specific sequence of that portion of peptides or proteins that bind to a receptor or target of interest, or mediate a biological activity of interest; and methods to determine the target-specific folding site within peptides and proteins.

2. Background Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Peptide and Protein Folding. Determination of the biologically relevant structure of proteins and peptides, which can be characterized as a functional three-dimensional structure, is a difficult problem in the biological, biochemical and pharmaceutical sciences. Through use of any of a variety of methods the primary structure of relevant peptides or proteins may be ascertained. That is, the sequence of amino acid residues composing the peptide or protein can be determined, and it is known that the peptide or protein has a desired biological effect, such as binding a target molecule or receptor of interest, mediating a biological activity of interest, or the like. However, both the three-dimensional structure and identification of the specific portion of the peptide or protein forming a ligand and thereby giving rise to the desired biological effect is frequently unknown.

Peptides and proteins are highly flexible, due in large part to the high rotational degrees of freedom of individual amino acid residues. In addition, some bonds in side chains of individual amino acid residues also have rotational degrees of freedom. The non-bonded steric interactions between amino acid residues force the peptide or protein along its degrees of freedom into some stable minimal free energy configuration. Local structures, also known as a "secondary structure," are common in peptides and proteins. These structures include α-helixes, β-bends, sheets, extended chains, loops and the like, and most often contribute to binding or receptor-specificity of peptides and proteins.

There are several types of α-helixes known, differing in torsion angles within the amino acid residues of the actual turn and by the patterns of intra- and inter-molecular hydrogen bonding. There are also a number of known different β-bends, differing in the dihedral torsion angles ψ (for the $C^{\alpha}$—C bond) or ϕ (for the $C^{\alpha}$—N bond), or both.

Peptide and protein folding are recognized as complex problems, involving consideration of all or virtually all the primary structure of the peptide or protein. Thus distal portions of a given molecule may significantly and substantially affect the secondary structure of a portion of the molecule of interest. For example, a six amino acid residue peptide may, as a distinct molecule, have a substantially different secondary and/or tertiary structure than would that same sequence as part of a larger peptide or protein.

A wide variety of mathematical, computational and others models have been developed for predicting the secondary structure of proteins and the secondary and tertiary structure of peptides, but no model gives satisfactory responses under other than the most limited circumstances. For example, software modeling programs (e.g., such as those distributed by Tripos, Inc., Pharmacopeia Inc. and the like), depend on various algorithms, statistical tools, assumed relationships between groups and the like, any or all of which may not be valid for any given protein or peptide. A number of methods are described in the art, such as those disclosed in International Publication No. WO 00/23564 to Xencor, Inc., International Publication Nos. WO 00/57309 and WO 01/35316, both to Structural Bioinformatics, Inc., International Publication No. WO 01/50355 to Structural Bioinformatics Advanced Technologies A/S, International Publication No. WO 01/59066 to Xencor, Inc., U.S. Pat. No. 6,278,794 to Parekh et al., and U.S. Patent Application No. 2001/0000807 to Freire and Luque.

Generation of structure-based pharmacophores, utilizing experimental methods such as X-ray crystallography or NMR, optionally in conjunction with protein structure determination methods, such as homology modeling, is known in the art. However, in order for this approach to be employed it must be possible to obtain appropriate data from the ligand in the conformation specific for the receptor defining the pharmacophore. In many, if not most, instances this is not feasible.

It may be determined that a particular peptide or protein sequence, with a length between about five residues to about fifty or more residues, binds to a particular receptor. However, the specific residues actually participating in binding, and the local secondary structure of the sequence which contains these specific residues, is not known. Without this knowledge, it is impossible to devise a systematic rational approach to make peptide-based drugs, peptidomimetic drugs or small molecule drugs. With knowledge of the specific residues and local secondary structure, it is possible to define the pharmacophore for the receptor. This definition may include, for example, the location in a three-dimensional construct of hydrogen bond donors and acceptors, positively and negatively charged centers, aromatic ring centers, hydrophobic centers and the like, such as described in terms of the distances between the atoms in the pharmacophore.

U.S. Pat. No. 5,834,250, to Wells et al., provides methods for the systematic analysis of the structure and function of polypeptides, specifically by identifying active domains by substituting a "scanning amino acid" for one of the amino acid residues within a suspected active domain of the parent polypeptide. These residue-substituted polypeptides are then assayed using a "target substance". In practice, a "scanning amino acid", such as alanine, is substituted for various residues in a polypeptide, and binding of the substituted polypeptide to a target substance compared to binding of the parent polypeptide. Similarly, U.S. Pat. No. 6,084,066, to Evans and Kini, discloses homologs and analogs of naturally occurring polypeptides with "conformation-constraining moieties" flanking "interaction sites". However, this method requires that the "interaction site" or amino acid sequence be known. The "interaction site" sequence is then flanked on both termini with proline residues, which are asserted to stabilize interaction sites.

There is thus a significant and substantial need to develop methods for identifying the specific residues in a peptide which are involved in binding to a receptor of interest, and to identify the specific secondary structure of the residues involved in binding.

Metallopeptides. It is known that linear peptides have high rotational degrees of freedom, such that for even small peptides with known primary structures the theoretically possible secondary and tertiary structures may number in the millions. In general cyclic peptides are more constrained, and at least small cyclic peptides have far fewer theoretically possible secondary and tertiary structures. However, even with cyclic peptides it is frequently impossible to predict with precision the actual secondary structures present in such peptide. By contrast, metallopeptides have well-defined and limited secondary structures, with the residues involved in metal ion complexation forming a turn structure about the metal ion. The atoms forming a part of the coordination sphere of the metal ion are fixed by the coordination geometry of the metal ion. This, coupled with the peptide bonds between residues and the side chain bonds, yields a conformationally fixed and predictable secondary structure for at least the residues involved in metal ion complexation. U.S. Pat. No. 5,891,418, entitled Peptide-Metal Ion Pharmaceutical Constructs and Applications, U.S. Pat. No. 6,027,711, entitled Structurally Determined Metallo-Constructs and Applications, and P.C.T. Patent Application Serial No. PCT/US99/29743, Published Application No. WO 96/40293, entitled Metallopeptide Combinatorial Libraries and Applications, each teach aspects of making and using metallopeptides and mimetics thereof, and each of the foregoing is incorporated herein by reference. These patents and applications disclose receptor-specific metallopeptides and methods of making peptides and complexing the peptides to various metal ions.

There are methods for screening peptides for metal coordinating properties, such as disclosed in U.S. Pat. No. 6,083,758 to Imperiali and Walkup. However, these methods, which employ monitoring the fluorescence to detect metal coordination, do not provide any information regarding binding of metal coordinated peptides to receptors or targets of interest.

There is thus a need for identifying target-specific sequences within peptides and proteins, and is further a need for a knockout method, which by demonstrating decreased or changed binding or functionality of selected constructs elucidates the primary sequence involved in such binding or functionality.

SUMMARY OF THE INVENTION (DISCLOSURE OF THE INVENTION)

In one embodiment, the invention provides a method of determining the specific residues binding to a target of interest within a known parent polypeptide that binds to the target of interest, the method including the steps of:

(a) providing a known parent polypeptide that binds to a target of interest with a known primary structure, such primary structure consisting of n residues;

(b) constructing a first peptide of the formula $R_1$—Z—$R_2$, wherein $R_1$ comprises from 2 to n residues, such residues the same as or homologs of residues in the parent polypeptide and in the same order as residues in the parent polypeptide primary structure;

Z is a residue or mimetic thereof providing both an N and an S for metal ion complexation;

$R_2$ comprises from 0 to n−2 residues, such residues the same as or homologs of residues in the parent polypeptide and in the same order as residues in the parent polypeptide primary structure, and forming with $R_1$ a sequence in the same order as in the parent polypeptide primary structure with Z either inserted between two adjacent residues corresponding to two adjacent residues in such primary structure or substituting for a single residue corresponding to a single residue in such primary structure, and wherein the residues comprising $R_1$—Z—$R_2$ are equal to either n or n+1;

(c) complexing the first peptide of the formula $R_1$—Z—$R_2$ to a metal ion, thereby forming a first $R_1$—Z—$R_2$ metallopeptide;

(d) screening the first $R_1$—Z—$R_2$ metallopeptide for binding to the target of interest;

(e) repeating steps (b) through (d), wherein the resulting $R_1$—Z—$R_2$ metallopeptide differs in at least either $R_1$ or $R_2$; and (f) selecting the $R_1$—Z—$R_2$ metallopeptide exhibiting substantially decreased binding to the target of interest, whereby at least one residue of the sequence binding to the metal ion of such $R_1$—Z—$R_2$ metallopeptide comprises the identification of the specific residues of the parent polypeptide binding to the target of interest.

In this method, Z can be an L- or D-3-mercapto amino acid, including but not limited to L- or D-cysteine, L- or D-penicillamine, 3-mercapto phenylalanine, or a homolog of any of the foregoing. The metal ion can be any metal ion, including but not limited to an ion of V, Mn, Fe, Co, Ni, Cu, Zn, Ga, As, Se, Y, Mo, Tc, Ru, Rh, Re, Pd, Ag, Cd, In, Sn, W, Re, Os, Ir, Pt, Au, Hg, Tl, Pb, Bi, Po, At, Sm, Eu or Gd.

In this method, the target of interest can be a receptor, antibody, toxin, enzyme, hormone, nucleic acid, intracellular protein domain of biological relevance or extracellular protein domain of biological relevance. Screening for binding to the target of interest can include competing a known binding partner for binding to the target of interest with the $R_1$—Z—$R_2$ metallopeptide. The known binding partner can be the parent polypeptide. Screening for binding to the target of interest can include a functional assay. Thus the target of interest can be a biological receptor capable of transmitting a signal, and screening can further include determining whether a $R_1$—Z—$R_2$ metallopeptide exhibits decreased transmission of the signal.

It is a primary object of this invention to provide a series of metallopeptides incorporating a known peptide or protein primary sequence, wherein the metal ion complexation sequence is varied in position based upon one or more amino acid residue substitution or insertion schemes, with identification of the endogenous site of biological binding or activity determined, in part, by the locus of the metal ion complexation sequence or sequences, which constitute a knockout or knockouts of the known primary sequence and which significantly or substantially inhibits biological activity.

Another object of this invention is to provide metallopeptide sequences, wherein the metallopeptides include a metal ion-complexing domain, such that a specific conformational secondary structural motif is obtained upon metal complexation.

Another object of this invention is to provide metallopeptide sequences, wherein each metallopeptide includes a metal ion-complexing domain in a distinct, known and different location within the sequence, wherein the metallopeptides may be exposed to a substance and one or more metallopeptides will exhibit decreased specificity and/or affinity for the substance.

Another object of this invention is to provide a method for identifying the specific residues within a known peptide that are involved in binding to a known target of interest.

Another object of this invention is to provide methods for synthesis of peptides wherein the peptides contain a single reactive —SH group forming a part of a metal ion-complexing domain, whereby the reactive —SH group is protected during synthesis, and is deprotected only upon complexing the peptide with a metal ion.

Another object of this invention is to provide a method for making metallopeptides as models for the active binding site in a known parent polypeptide, wherein each endogenous cysteine residue is substituted by another amino acid or, alternatively, wherein each endogenous cysteine residue further includes an S-protecting group, such that the sulfur of such endogenous cysteine does not form a part of a metal ion-complexing domain.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out herein.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

Figure 1:
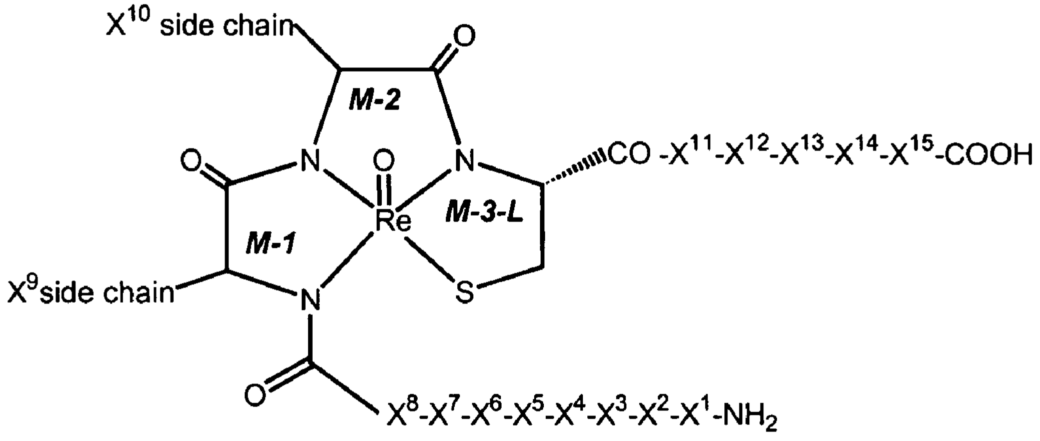
FIG. 1 illustrates the structure of a conceptualized L-Cys metallopeptide complexed to Re, wherein M-1 and M-2 are two amino acid residues involved in metal complexation along with the L-Cys (M-3-L) residue, and wherein the L-Cys is inserted in a parent peptide of the sequence $NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH.

DESCRIPTION OF THE PREFERRED EMBODIMENTS (BEST MODES FOR CARRYING OUT THE INVENTION)

Certain terms as used throughout the specification and claims are defined as follows:

The terms "bind," "binding," "label," "labeling," "complex," and "complexing," as used throughout the specification and claims are generally intended to cover all types of physical and chemical binding, reactions, complexing, attraction, chelating and the like.

The "polypeptides" and "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing polypeptides or peptides.

The term "polypeptide" as used throughout the specification and claims is intended to include any structure comprised of two or more amino acid residues, including chemical modifications and derivatives of amino acid residues. The term "polypeptides" thus includes a conventional "peptide" containing from two to about 20 amino acid residues, a conventional polypeptide with from about 20 to about 50 amino acid residues, and a conventional "protein" with a minimum of about fifty 50 amino acid residues. For the most part, the polypeptides made according to this invention and utilized as metallopeptides comprise fewer than 100 amino acid residues, and preferably fewer than 60 amino acid residues, and most preferably ranging from about 5 to 20 amino acid residues. The amino acid residues forming all or a part of a polypeptide may be naturally occurring amino acid residues, stereoisomers and modifications of such amino acid residues, non-protein amino acid residues, post-translationally modified amino acid residues, enzymatically modified amino acid residues, constructs or structures designed to mimic amino acid residues, and the like, so that the term "polypeptide" includes pseudopeptides and peptidomimetics, including structures which have a non-peptidic backbone. A "manufactured" peptide or polypeptide includes a peptide or polypeptide produced by chemical synthesis, recombinant DNA technology, biochemical or enzymatic fragmentation of larger molecules, combinations of the foregoing or, in general, made by any other method.

The "amino acid residues" used in this invention, and the term as used in the specification and claims, include the known naturally occurring coded protein amino acid residues, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid residue" also includes stereoisomers and modifications of naturally occurring protein amino acid residues, non-protein amino acid residues, post-translationally modified amino acid residues, enzymatically synthesized amino acid residues, derivatized amino acid residues, constructs or structures designed to mimic amino acid residues, and the like. Modified and unusual amino acid residues are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. A single amino acid residue, or a derivative thereof, is sometimes referred to herein as a "residue" or as an "amino acid." In addition, the following abbreviations have the meanings giving:

| | |
|---|---|
| Ac | acetyl |
| Nle | norleucine |
| D-Phe | D-phenylalanine |
| Pyr | pyroglutamic acid |

The constructs of this invention also include a metal ion, which may be an ionic form of any element in metallic form, including but not limited to metals and metalloids. The metal ion may, but need not, be radioactive, paramagnetic or superparamagnetic. The metal ion can be of any oxidation state of any metal, including oxidation states of vanadium (V), manganese (Mn), iron (Fe), cobalt (Co), nickel (Ni), copper (Cu), zinc (Zn), gallium (Ga), arsenic (As), selenium (Se), yttrium (Y), molybdenum (Mo), technetium (Tc), ruthenium (Ru), rhodium (Rh), palladium (Pd), silver (Ag), cadmium (Cd), indium (In), tin (Sn), tungsten (W), rhenium (Re), osmium (Os), iridium (Ir), platinum (Pt), gold (Au), mercury (Hg), thallium (Tl), lead (Pb), bismuth (Bi), polonium (Po), astatine (At), samarium (Sm), europium (Eu), and gadolinium (Gd). The metal ion can also be a radionuclide of any of the foregoing, including In, Au, Ag, Hg, Tc, Re, Sn, At, Y and Cu. A preferred metal ion with a tetradentate coordination sphere is Re. For applications wherein a radioisotope is desirable for screening or in assay systems, an alpha-, gamma- or beta-emitting radionuclide may be employed.

In one embodiment, the method of the invention provides for the systematic analysis of a parent polypeptide to determine at least one active sequence or domain in the parent polypeptide that is involved in the interaction, such as binding, of the parent polypeptide with a target substance. As used herein, "parent polypeptide" refers to any sequence of amino acid residues that exhibits interaction, such as binding, to a target substance, and which may thus constitute a peptide, a polypeptide or a protein. The parent polypeptide is generally a polypeptide as defined herein, with from about 5 to about 100 amino acid residues, but the term parent polypeptide can also include larger constructs, generally considered in the art to be large polypeptides or proteins. To employ the method of the invention, the primary structure, which is to say the sequence, of preferably all of the parent polypeptide must be known. However, it is not necessary to have any information concerning the secondary or tertiary structure of the parent polypeptide in order to practice the method of the invention.

The parent polypeptide may be any sequence that exhibits binding to a receptor found on, for example, cells, tissues, organs or other biological materials. Examples of parent polypeptides include, without limitation, biologically active peptides, hormones, neurotransmitters, enzymes, antibodies and the like. Such parent polypeptides may transmit signals, directly or indirectly, as a result of binding to a receptor, and thus a parent polypeptide may be an agonist, an antagonist, or a mixed agonist-antagonist. Examples of suitable parent polypeptides of the invention include melanocortin-receptor specific peptides, urokinase-type tissue plasminogen activator protein, amyloid beta-protein related peptides, prion disease related peptides, vasopressin peptides, oxytocin peptides, angiotensin peptides, calcitonin, calcitonin gene related peptide, bradykinin, cholecystokinin, urotensin, bombesin, neuromedin B, gastrin releasing peptide, atrial naturetic peptide, somatostatin, opioid peptides, human growth hormone, human prolactin receptor ligands, various interferons such as alpha-interferon, epidermal growth factor, tumor necrosis factor, and various hypotensive peptides, fibrinolytic peptides, chemotactic peptides, growth promoter peptides, mitogens, immunomodulators and the like.

In general, in order to employ the invention at least one assay or test to determine binding or functionality of the constructs of the invention to a receptor of interest, and preferably to also determine binding or functionality of the parent polypeptide to a receptor of interest, must be known. In a preferred embodiment of the invention, a competitive inhibition or similar assay is employed, whereby the binding or functional activity of a construct of the invention can be directly compared to the parent polypeptide, and relative binding or functional activity thus directly determined. In other embodiments other assays or tests may be employed. These assays may, but need not, be functional assays. Examples of assays include any of a variety of competitive inhibition assays, direct binding assays, functional assays, and the like. It is also possible and contemplated to employ assays that determine, for example, whether a construct of the invention is an agonist, antagonist or mixed agonist-antagonist, and further where binding and function can separately be determined, to independently determine both receptor affinity and specificity as well as functional activity. Examples of such assays and tests are well known and well documented in the art, and in general one or more such assays or tests are known for any parent polypeptide.

In a method of the invention, the parent polypeptide is employed as the template for generation of one or more, and preferably of a series, of peptides that are then complexed to a metal ion. In a preferred embodiment, the generated peptides are of the same length, or the same length plus one residue, as the parent polypeptide. The generated peptide is complexed to a metal ion, thereby forming a metallopeptide. The metallopeptide is then employed in any of a variety of known or new assays or tests, and the binding or function, or both, of the metallopeptide compared to that of the parent polypeptide.

The target-specific site in the parent polypeptide can be tentatively identified as the residues wherein binding or function is most inhibited upon complexation of such residues to a metal ion. In general, complexation of a metal ion to a series of residues (such as, e.g., a series of three residues forming an $N_3S_1$ complexation system) fixes such series in a known, specific and extremely rigid secondary structure, such that the resulting structure is fixed. The coordination sphere of various common metal ions, in general, is tetradentate to hexadentate. In one embodiment according to this invention, residues are included within each generated peptide such that the peptide contains a three- or four-residue sequence containing the desired number of groups (4 to 6 in most cases) for complexing with the metal. As a result, upon complexing with a metal, the resulting metallopeptide forms a secondary structural motif about the site of metal complexation. A metal with coordination number 4, 5 or 6, and complexing respectively with an amino acid sequence forming a tetra, penta, or hexadentate ligand, will fold and constrain the ligand. A highly flexible molecule like a peptide, in other words, is folded to form a local secondary structural motif upon its complexation with a metal ion. This resulting motif is a highly constrained structure in the conformational sense.

If the highly constrained local secondary structural motif is different than the corresponding native structural secondary motif in the parent polypeptide necessary for binding or function, then binding or function will be inhibited. This inhibition may be employed to identify the specific sequence within the parent polypeptide responsible for biological activity, such as binding or function, by sequentially modifying the parent polypeptide to form a highly constrained local secondary structure resulting from metal ion complexation at different positions along the sequence of the parent polypeptide.

Figure 4:
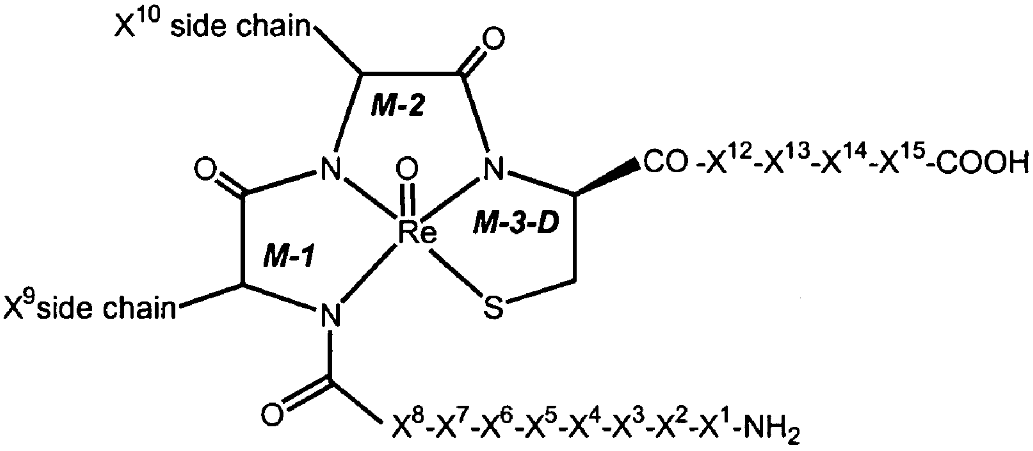
FIG. 4 illustrates the structure of a conceptualized D-Cys metallopeptide complexed to Re, wherein M-1 and M-2 are two amino acid residues involved in metal complexation along with the D-Cys (M-3-D) residue, and wherein the D-Cys is substituted for a single amino acid residue, $X^{11}$, in the parent peptide of the sequence $NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH.
Figure 5:
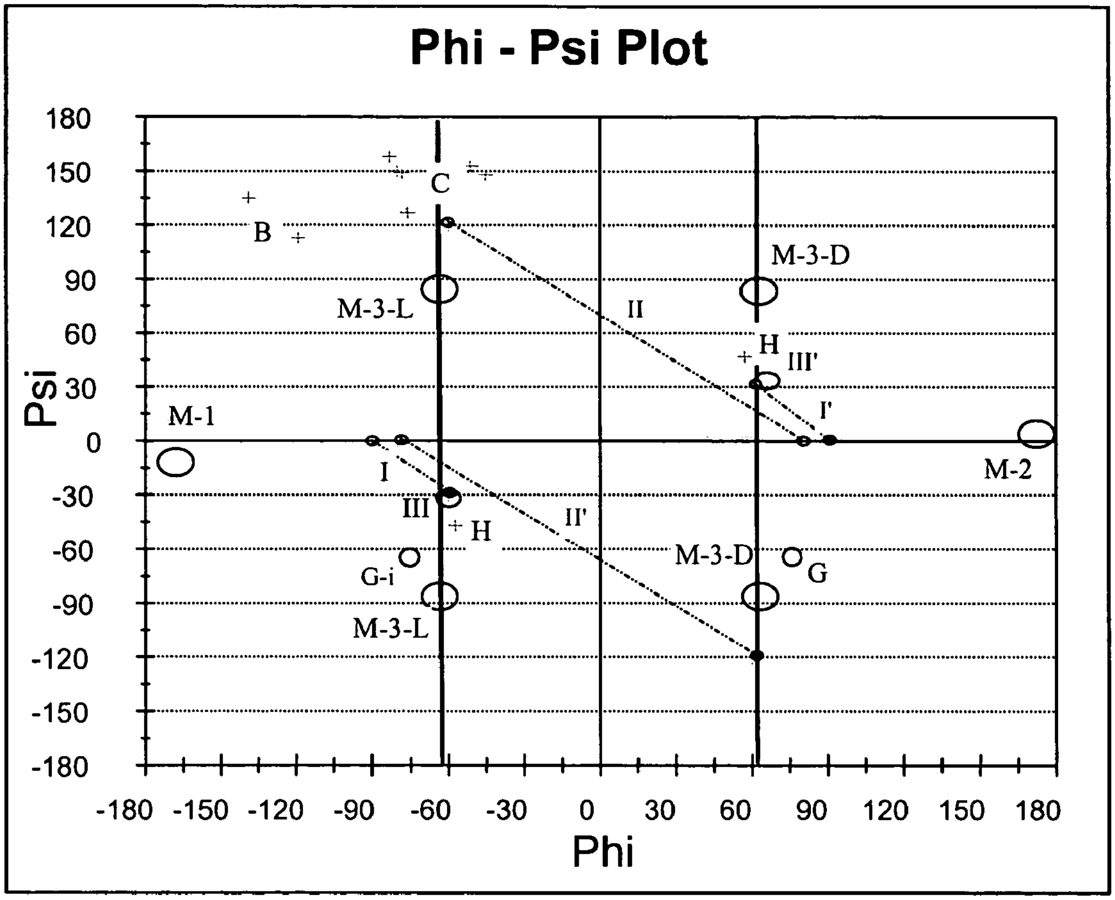
FIG. 5 is a phi-psi (Ramachandran) plot of the metallopeptide core sequence of FIGS. 1 to 4 showing coordinates (structural propensity) for M-1, M-2, M-3-L, and M-3-D residues. Also included in the plot are the regions of natural protein structures such as an α-helix (H), β-sheet (B), collagen helix (C), gamma turn (G), inverse gamma turn (G-i), type-1-beta turn (I), type-1'-beta-turn (I'), type-II-beta-turn (II), type-II'-beta-turn (II'), type-III-beta-turn (III) and type-III'-beta-turn (III'). A dashed line defining an amino acid pair (i+1 and i+2 residues) of a turn structure is shown. The H with negative phi and psi values is for a natural right handed helix, while the other H with positive phi, psi values represents a left handed helix. The M-1 and M-2 residues reside near the 0°, 180° or 0°, −180° coordinates. Both positions indicate that these amino acid residues in these metallopeptides represent a structure different then any of the natural protein structures. The phi angle in L-Cys (M-3-L) or D-Cys (M-3-D) is fixed at approximately −63° and +63° respectively (two solid vertical lines). Based on the psi value of Cys residues, M-3-L and M-3-D lies somewhere on these two vertical lines. However, due to the restricted orientation of the carbonyl (CO) group of either Cys residue, the psi angle ranges from 60° to 90° or −60° to −90° for L- and D-Cys, respectively. Under these conditions it is evident from the Ramachandran plot that the conformational characteristics at Cys fall close to a right-handed helix region for L-Cys and a left-handed helix region for D-Cys.

Metal ion complexation with rhenium results in a specific turn structure, identified in the Ramachandran phi-psi plot, as shown in FIG. 5. The Ramachandran plot of FIG. 5 shows the coordinates, and thus corresponding structural propensity, of the M-1, M-2, M-3-L, and M-3-D residues of the metallopeptide cores of the structures of FIGS. 1 to 4. It can thus be seen that a metallopeptide with an L-Cys forms a mimic of a short right hand turn of s helix, while a metallopeptide with a D-Cys forms a mimic of a short left hand turn of a helix. It is well know that natural helix turns are right-handed only. The metallopeptide approach, therefore, offers the advantage that both right- and left-handed structures can be constructed. These structure can be utilized to topographically position the side chains of i and i+5 residues in a L-Cys containing metallopeptide in the same chemical space as that for the side chains of and i+4 residues in a right handed helix. Alternatively, a D-Cys containing metallopeptide allows creation of a topographic mimic for i and i+4 residues of a putative un-natural left helix.

It is also to be appreciated that while the natural and linear peptide and analogues are subjected to the confines of the Chou-Fasman type of rules (P Y Chou and G D Fasman: Prediction of protein structure. *Biochemistry* 13:222-245, 1974) that preclude inclusion of certain amino acid residues in particular types of secondary structures, the methods and constructs of this invention are completely independent of these rules. This invention allows incorporation of any natural or synthetic amino acid residues in the structure without Chou-Fasman rules limitations, and with virtually no other limitations.

It is to be appreciated here that while the structures shown in FIGS. 1 to 4 have backbones that are very distinct from those in natural protein structures, one objective of this invention is to utilize the similarities in terms of positioning C-α carbon atoms, as well as C-β carbon atoms in certain cases, of various amino acid residues in the same chemical spaces as in corresponding native protein structures. Utilizing these metallopeptide structures that include all or substantially all the residues found in a biologically active parent peptide, biologically inactive molecules can be identified that represent and define metal ion complexation, and/or steric hindrance at other binding components, by means of inducing a specific turn at a biologically critical locus along the parent peptide. This identification of critical amino acid residues thus elucidates the residues necessarily involved in a folding site or other biologically active structure in the polypeptide.

Once a specific sequence is identified, it is possible to use the methods of International Application No. PCT/US01/50075, published as International Published Application No. WO 02/064734, incorporated herein by reference, to make smaller sequence metallopeptides, comprising only the identified amino acid residues, and optionally from one to about three residues on either the N-terminus or C-terminus ends of the identified amino acid residues. The resulting smaller metallopeptides provide information on key constrained amino acid residues, including but not limited to their relationship, including spatial relationship, to one another, and their chirality. This information can then utilized to generate a molecular model, such as a computer-based molecular model, that defines a minimal structure pharmacophore model for further optimization. In the practice of this invention it is possible to utilize structural motifs thus identified by further modification of the defined topology to accentuate a desired biological effect, such as by substituting homologous amino acid side chains in place of naturally-occurring side chains in the parent polypeptide. Examples of homologous side chains include, but are not limited to, substituting a D-amino acid residue for an L-amino acid residue or utilizing homologs of an amino acid, such as for example the series phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like.

As is taught in PCT/US01/50075, in the event that the resulting specific turn structure is a mimic of the native or endogenous turn structure in the parent polypeptide, then the resulting metallopeptide may be employed as a pharmaceutical agent itself, or may be used as a template to define a shape space to model a small molecule. As is taught in that application, it is preferred to "divide" the parent polypeptide into small sequences, modified as required by insertion or substitution of an $N_1S_1$, residue, and test each resulting metallopeptide. Thus, for example, a parent polypeptide of 15 residues length might be divided into a series of metallopeptides, each of 4 residues length.

Applicant has unexpectedly and surprisingly found that metallopeptide formation may be employed to identify the portion or sequence within a parent polypeptide responsible for biological activity such as binding or function by essentially forming "knockout" metallopeptides, wherein the position of the metal complexation site is varied step-wise by residue through the primary structure, with identification of the key sequence implicated in biological activity by determination of the metallopeptide with least binding. The active pharmacophore in the metallopeptide is preserved, with concomitant biological activity, in the instances wherein the metal complexation site does not disrupt or interfere with the active pharmacophores. Thus the method disclosed herein involves use of metal complexation to eliminate or knock out the active pharmacophores, where prior methods, such as that disclosed in PCT/US01/50075, utilizes metal complexation to stabilize the active pharmacophore in a preferred three-dimensional configuration, such that the resulting metallopeptide is a mimic of the active pharmacophores, and binds to the receptor or target of interest.

It may readily be seen that the approach described in this invention is particularly efficacious where the three-dimensional conformation of the metal complexation site is not a close mimic of the three-dimensional conformation, which is to say the secondary structure, of the sequence within a parent polypeptide responsible for biological activity such as binding or function. For example, use of a D-Cys for insertion or substitution in a parent polypeptide might result in a biologically inactive metallopeptide, as compared to use of an L-Cys for insertion or substitution, thereby in part defining both the specific amino acid residues implicated in binding or function, as well as the spatial orientation of side chains thereof. It is also possible and contemplated that even if the three-dimensional conformation resulting from metal complexation is a close mimic of an active pharmacophore, the resulting metallopeptide may nonetheless be biologically inactive or exhibit decreased biological activity due to global or tertiary structure effects resulting from metal complexation. For example, one or more auxiliary elements, such as a hydrogen bond donor or acceptor, positively or negatively charged center, aromatic ring center, hydrophobic center or the like may be involved in biological activity, but nonetheless distal by one or more residues from the primary pharmacophore, and may as a result of metal complexation not be sterically available. This may thus be considered a form of steric hindrance. If, in fact, the three-dimensional conformation of the metal complexation site is a close mimic and does not result in steric hindrance of other auxiliary elements required for biological activity, then the methods of PCT/US01/50075 may readily be employed. However, if the method of PCT/US01/50075 does not yield determination of the specific desired three-dimensional conformation, then the method as disclosed in this application may be employed.

In one preferred embodiment of the invention, the regional secondary structure of that portion of a peptide, polypeptide, or protein, and in general any molecule or molecular structure incorporating amino acid residues or mimetics thereof, binding to any receptor or target of interest is defined by means of the methods and constructs hereafter provided.

The present invention employs to advantage the unique structures and characteristics of metallopeptides formed by complexing a metal ion to two or more amino acid residues, and in a preferred embodiment, to three amino acid residues. For most metal ions, including for example ions of Re, Tc, Cu, Ni, Au, Ag, Sn and Hg, a complex to a contiguous series of three amino acid residues which include therein at least one available sulfur atom (S) is preferred. In a preferred embodiment, there is one available S in the contiguous series of three amino acid residues. That is, metal ions, provided that such ions are in the appropriate and desired oxidation state for complexing, will preferably complex to a tri-peptide sequence including a residue with an S available for complexing, and most preferably a residue including both an S and a nitrogen atom (N) available for complexing, in preference to tri-peptide sequences wherein no S is available for complexing.

For example, it may thus be seen that in any amino acid sequence of length n, where n is at least 3, metal ions in the appropriate and desired oxidation state will preferentially complex to a tri-peptide sequence $A^1$-$A^2$-Cys, where each of $A^1$ and $A^2$ is independently any amino acid residue other than Pro or Cys, and further provided that the only Cys (or other residue with an S available for complexing) present in the amino acid sequence of length n is the Cys in $A^1$-$A^2$-Cys. Here Cys, as well as $A^1$ and/or $A^2$, may be of L- or D-configuration. The dynamics of the metal complexation reaction is such that the preferred resulting metallopeptide includes, for a tetradenate metal ion, an $N_3S_1$ ligand, formed of the tri-peptide sequence $A^1$-$A^2$-Cys. With more than one Cys residue, or mimetic or variation of a Cys residue providing both an N (nitrogen) and S (sulfur) atom, the structure of the resulting metallopeptide is difficult to predict, and a variety of species of metallopeptides may result from complexing with a metal ion. For example, an amino acid sequence of length n containing two Cys residues may cross-link, dimerize, polymerize, form internal disulfide bridges and the like. In terms of metal complexation, there may, depending on the primary structure of the sequence, be at least two different sites of metal ion complexation, such that some molecules will have a metal ion bound to a first site, others to a second site and still others to both sites. Thus the structure of a resulting metallopeptide with two or more Cys residues cannot be predicted, and must be empirically determined. Similarly, it is also possible, again depending on the primary structure of the sequence, that one or more sites in the sequence will provide an $N_3S_1$ ligand, while at least one other site in the sequence will provide an $N_2S_2$ ligand. Here too the structure of the resulting metallopeptide cannot be predicted, and must be empirically determined. In general, as discussed hereafter, such results may be prevented in an amino acid sequence containing more than one Cys residue by utilizing an appropriate protecting group such that the S in one or more selected Cys residues is not available for metal ion complexation, or by substituting such Cys with another residue, preferably a homolog as hereafter defined which does not provide an S for metal ion complexation.

The present invention encompasses a method for defining, at least in part, the secondary structure of a region of a peptide, polypeptide, or protein, or in general any molecule or molecular structure incorporating amino acid residues or mimetics thereof, that binds to any receptor or target of interest. This is accomplished by substitution or insertion of a Cys residue, or other residue, mimetic, or homolog providing both an N and S for complexation to the coordination sphere of a metal ion (an "$N_1S_1$ residue"), at each available positions along the molecule, complexing a metal ion thereto to form a metallopeptide, and testing the resulting metallopeptide for binding to the receptor or target of interest. In one embodiment of the invention, the primary structure of a parent polypeptide, such as a peptide, polypeptide or protein binding to a receptor or target of interest, is known. Such parent polypeptide is composed of some specific number of residues, referred to as n residues. A series of peptides of the formula $R_1$—Z—$R_2$ is made, wherein $R_1$ is from 2 to n residues that are the same as or homologs of residues in the parent polypeptide and in the same order as in the parent polypeptide. Z is any $N_1S_1$ residue, including but not limited to L-Cys, D-Cys, L-Pen, D-Pen or 3-mercapto phenylalanine. $R_2$ is from 0 to n−2 different residues that are the same as, or homologs of, residues in the known primary structure in the same order as in the parent polypeptide. Further, $R_1$ and $R_2$ together constitute at least two residues, and together form a sequence in the same order as in the parent sequence where Z is either inserted between two adjacent residues or substitutes for a single residue. Preferably $R_1$ and $R_2$ together are equal to n in the event of an insertion, and equal to n−1 in the event of a substitution. Any Cys in $R_1$ or $R_2$ may be conservatively substituted with Gly, Ala or Ser (among naturally occurring coded protein amino acid residues), and preferably Gly or Ala. Alternatively, a Cys with an S-protecting group (as hereafter described) may be employed. In a further embodiment, any synthetic or unnatural relatively small, neutral amino acid may be employed, for example amino isobutyric acid (Aib), 1-amino, 1-cyclopentane carboxylic acid, or dehydroalanine (ΔAla). Any Pro in the two residues on the immediately adjacent amino-terminus side of Z is located in a position that forms a part of the putative metal ion complexation tri-peptide sequence, and is similarly conservatively substituted. Such substitution is required because there is no available N in Pro to complex to the coordination sphere of a metal ion, and therefore Pro cannot form a part of a metal ion complexation tri-peptide sequence. Accordingly, any such Pro may be substituted with Gly, Ala or Ser (among naturally occurring coded protein amino acid residues), and preferably Gly or Ala. In a further embodiment, any synthetic or unnatural relatively small, neutral amino acid may be employed, for example Aib, 1-amino, 1-cyclopentane carboxylic acid, or ΔAla.

As used herein, the term "homolog" includes, in the case of a Cys to be substituted as set forth above, a conservative substitution with Gly, Ala or Ser, and preferably Gly or Ala. The term "homolog" further includes a Cys with an S-protecting group, wherein because of the S-protecting group the sulfur in the Cys residue is no longer available for binding to a metal ion. The terms "homolog" further includes, in the case of a Cys to be substituted, any synthetic or unnatural relatively small, neutral amino acid, for example Aib, 1-amino, 1-cyclopentane carboxylic acid, or ΔAla. In the case of a Pro to be substituted as set forth above, the term "homolog" includes a conservative substitution with Gly, Ala or Ser, and preferably Gly or Ala. The terms "homolog" further includes, in the case of a Pro to be substituted, any synthetic or unnatural relatively small, neutral amino acid, for example Aib, 1-amino, 1-cyclopentane carboxylic acid, or ΔAla. In the case of residues in either $R_1$ or $R_2$, other than Pro in the two residues on the immediately adjacent amino-terminus side of Z or Cys, a "homolog" of such residue includes (a) a D-amino acid residue substituted for an L-amino acid residue, (b) a post-translationally modified residue, (c) a non-protein amino acid or other modified amino acid residue based on such residue, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue, coded or otherwise, or a construct or structure that mimics an amino acid residue, which has a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

One a knockout sequence has been identified, which exhibits decreased binding or functionality, it is possible to employ the methods of PCT/US01/50075 to make smaller sequence metallopeptides, comprising only the identified amino acid residues, and optionally from one to about three residues, and preferably no more than two, on either the N-terminus or C-terminus ends of the identified amino acid residues. In brief, the identified knockout region is selected, comprising the amino acid residues involved in metal ion complexation, and optionally one or two adjacent residues. The pharmacophore can then be further elucidated by making metallopeptides consisting of those sequences, substituting an L-Cys for a D-Cys, substitution of side chains, and other similar modifications, to further define the pharmacophre.

In a preferred embodiment, the parent polypeptide is treated as a single unit. Assume, by way of example, a peptide of fifteen amino acid residues, i.e., where n is 15, binds to a specified known receptor. The peptide may be described as:

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH

In this parent polypeptide, X may be any residue, which residue may repeat multiple times in any order or sequence. Thus the residue in position $X^1$ may be different from or the same as the residue in position $X^2$, which may be different from or the same as the residues in position $X^1$ or $X^3$, and so on. Here too when a Cys is present in the parent polypeptide, substitution may be made. Similarly, where a Pro is present that comprises a part of the putative metal ion complexation tri-peptide sequence, such as when a Pro falls within the two residues in $R_1$ immediately adjacent the amino-terminus side of the $N_1S_1$ residue hereafter provided, substitution may be made.

In the practice of this invention, an $N_1S_1$ residue, providing both an N and an S for complexing to a metal ion, is employed, such as L- or D-cysteine, or any other natural, unnatural or synthetic amino acid or mimetic providing both an N and S for complexing to a metal ion. For the following examples, "Cys" is employed, it being understood that any $N_1S_1$ residue could be similarly employed, and that this example and those that follow are not limited to Cys as the $N_1S_1$ residue. Peptides are constructed using standard peptide synthesis techniques, in which the cysteine is inserted after the 2nd position ($X^2$) through the 16th (n+1) position (following $X^{15}$), such that the following peptides result:

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH (Parent)

$NH_2$—$X^1$—$X^2$-Cys-$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH (Insert. 1)

$NH_2$—$X^1$—$X^2$—$X^3$-Cys-$X^4$—$X^5$—$X^6$—$X^7$—$X^8$—$X^9$—$X^{10}$—$X^{11}$—$X^{12}$—$X^{13}$—$X^{14}$—$X^{15}$—COOH (Insert. 2)

$NH_2$—$X^1$—$X^2$—$X^3$—$X^4$-Cys-$X^5$-$X^6$—$X^7$—$X^8$—$X^9$—$X^{10}$—$X^{11}$—$X^{12}$—$X^{13}$—$X^{14}$—$X^{15}$—COOH (Insert. 3)

$NH_2$—$X^1$—$X^2$—$X^3$—$X^4$—$X^5$-Cys-$X^6$—$X^7$—$X^8$—$X^9$—$X^{10}$—$X^{11}$—$X^{12}$—$X^{13}$—$X^{14}$—$X^{15}$—COOH (Insert. 4)

$NH_2$—$X^1$—$X^2$—$X^3$—$X^4$—$X^5$—$X^6$-Cys-$X^7$—$X^8$—$X^9$—$X^{10}$—$X^{11}$—$X^{12}$—$X^{13}$—$X^{14}$—$X^{15}$—COOH (Insert. 5)

$NH_2$—$X^1$—$X^2$—$X^3$—$X^4$—$X^5$—$X^6$—$X^7$-Cys-$X^8$—$X^9$—$X^{10}$—$X^{11}$—$X^{12}$—$X^{13}$—$X^{14}$—$X^{15}$—COOH (Insert. 6)

$NH_2$—$X^1$—$X^2$—$X^3$—$X^4$—$X^5$—$X^6$—$X^7$—$X^8$-Cys-$X^9$—$X^{10}$—$X^{11}$—$X^{12}$—$X^{13}$—$X^{14}$—$X^{15}$—COOH (Insert. 7)

$NH_2$—$X^1$—$X^2$—$X^3$—$X^4$—$X^5$—$X^6$—$X^7$—$X^8$—$X^9$-Cys-$X^{10}$—$X^{11}$—$X^{12}$—$X^{13}$—$X^{14}$—$X^{15}$—COOH (Insert. 8)

$NH_2$—$X^1$—$X^2$—$X^3$—$X^4$—$X^5$—$X^6$—$X^7$—$X^8$—$X^9$—$X^{10}$-Cys-$X^{11}$—$X^{12}$—$X^{13}$—$X^{14}$—$X^{15}$—COOH (Insert. 9)

$NH_2$—$X^1$—$X^2$—$X^3$—$X^4$—$X^5$—$X^6$—$X^7$—$X^8$—$X^9$—$X^{10}$—$X^{11}$-Cys-$X^{12}$—$X^{13}$—$X^{14}$—$X^{15}$—COOH (Insert. 10)

$NH_2$—$X^1$—$X^2$—$X^3$—$X^4$—$X^5$—$X^6$—$X^7$—$X^8$—$X^9$—$X^{10}$—$X^{11}$—$X^{12}$-Cys-$X^{13}$—$X^{14}$—$X^{15}$—COOH (Insert. 11)

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$-Cys-$X^{14}$—$X^{15}$—COOH (Insert. 12)

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$-Cys-$X^{15}$—COOH (Insert. 13)

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$-Cys-COOH (Insert. 14)

Figure 2:
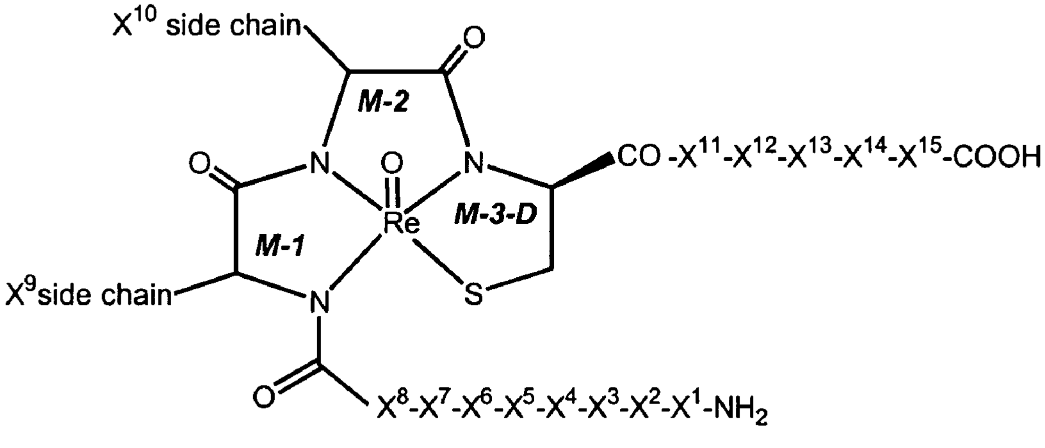
FIG. 2 illustrates the structure of a conceptualized D-Cys metallopeptide complexed to Re, wherein M-1 and M-2 are two amino acid residues involved in metal complexation along with the D-Cys (M-3-D) residue, and wherein the D-Cys is inserted in a parent peptide of the sequence $NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH.

In this way each potential insertion point along the parent polypeptide is "scanned" to determine if creation of a metal ion-stabilized secondary structural motif at each insertion point results in a metallopeptide with decreased biological activity, however defined. The resulting metallopeptide structure on metal ion complexation is illustrated in FIGS. 1 and 2 for insertion of an L-Cys and D-Cys residue, respectively, for Insert. 10. It may readily be seen that any of the metallopeptide structures listed above may be similarly depicted.

In an alternative embodiment employed in the practice of this invention, a substitution scheme may be employed, wherein "Cys" (which may be any $N_1S_1$ residue as discussed above), is substituted for an amino acid residue in a sequential or step-wise fashion. Thus, for example the following may result:

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH (Parent)

$NH_2$—$X^1$—$X^2$-Cys-$X^4$—$X^5$—$X^6$—$X^7$—$X^8$—$X^9$—$X^{10}$—$X^{11}$—$X^{12}$—$X^{13}$—$X^{14}$—$X^{15}$—COOH (Subst. 1)

$NH_2$—$X^1$—$X^2$—$X^3$-Cys-$X^5$—$X^6$—$X^7$—$X^8$—$X^9$—$X^{10}$—$X^{11}$—$X^{12}$—$X^{13}$—$X^{14}$—$X^{15}$—COOH (Subst. 2)

$NH_2$—$X^1$—$X^2$—$X^3$—$X^4$-Cys-$X^6$—$X^7$—$X^8$—$X^9$—$X^{10}$—$X^{11}$—$X^{12}$—$X^{13}$—$X^{14}$—$X^{15}$—COOH (Subst. 3)

$NH_2$—$X^1$—$X^2$—$X^3$—$X^4$—$X^5$-Cys-$X^7$—$X^8$—$X^9$—$X^{10}$—$X^{11}$—$X^{12}$—$X^{13}$—$X^{14}$—$X^{15}$—COOH (Subst. 4)

$NH_2$—$X^1$—$X^2$—$X^3$—$X^4$—$X^5$—$X^6$-Cys-$X^8$—$X^9$—$X^{10}$—$X^{11}$—$X^{12}$—$X^{13}$—$X^{14}$—$X^{15}$—COOH (Subst. 5)

$NH_2$—$X^1$—$X^2$—$X^3$—$X^4$—$X^5$—$X^6$—$X^7$-Cys-$X^9$—$X^{10}$—$X^{11}$—$X^{12}$—$X^{13}$—$X^{14}$—$X^{15}$—COOH (Subst. 6)

$NH_2$—$X^1$—$X^2$—$X^3$—$X^4$—$X^5$—$X^6$—$X^7$—$X^8$-Cys-$X^{10}$—$X^{11}$—$X^{12}$—$X^{13}$—$X^{14}$—$X^{15}$—COOH (Subst. 7)

$NH_2$—$X^1$—$X^2$—$X^3$—$X^4$—$X^5$—$X^6$—$X^7$—$X^8$—$X^9$-Cys-$X^{11}$—$X^{12}$—$X^{13}$—$X^{14}$—$X^{15}$—COOH (Subst. 8)

$NH_2$—$X^1$—$X^2$—$X^3$—$X^4$—$X^5$—$X^6$—$X^7$—$X^8$—$X^9$—$X^{10}$-Cys-$X^{12}$—$X^{13}$—$X^{14}$—$X^{15}$—COOH (Subst. 9)

$NH_2$—$X^1$—$X^2$—$X^3$—$X^4$—$X^5$—$X^6$—$X^7$—$X^8$—$X^9$—$X^{10}$—$X^{11}$-Cys-$X^{13}$—$X^{14}$—$X^{15}$—COOH (Subst. 10)

$NH_2$—$X^1$—$X^2$—$X^3$—$X^4$—$X^5$—$X^6$—$X^7$—$X^8$—$X^9$—$X^{10}$—$X^{11}$—$X^{12}$-Cys-$X^{14}$—$X^{15}$—COOH (Subst. 11)

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$-Cys-$X^{15}$—COOH (Subst. 12)

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$-Cys-COOH (Subst. 13)

Figure 3:
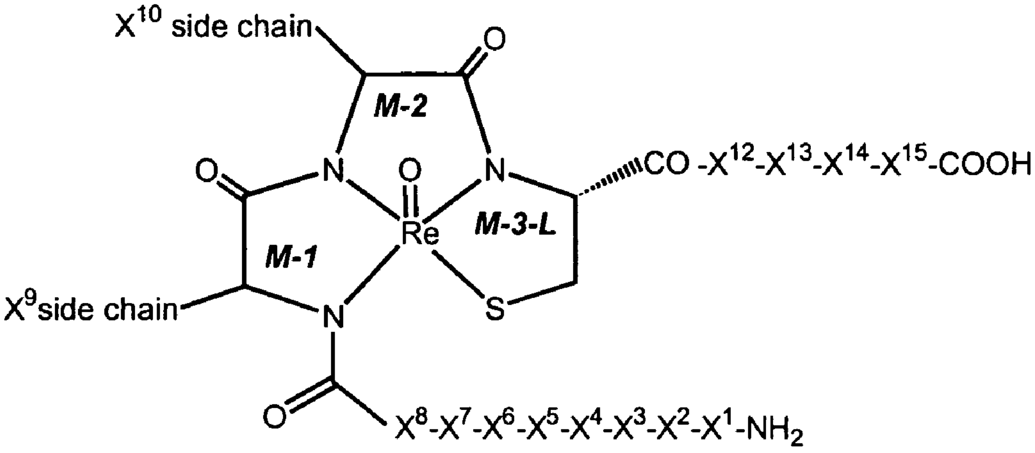
FIG. 3 illustrates the structure of a conceptualized L-Cys metallopeptide complexed to Re, wherein M-1 and M-2 are two amino acid residues involved in metal complexation along with the L-Cys (M-3-L) residue, and wherein the L-Cys is substituted for a single amino acid residue, $X^{11}$, in the parent peptide of the sequence $NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH.

The resulting metallopeptide structure on metal ion complexation is shown in FIGS. 3 and 4 for substitution of $X^{11}$ (Subst. 9) with an L-Cys and D-Cys residue, respectively, for a residue in the parent peptide. It may readily be seen that any of the metallopeptide structures listed above may be similarly depicted.

As may be seen from the examples, in many instances a majority of metallopeptides exhibit binding or other activity similar to that of the parent polypeptide, but that one, two or more metallopeptides may exhibit substantially and significantly decreased binding. By way of example, Inserts. 1 to 8 might exhibit binding between 80% and 100% of that exhibited by the parent polypeptide, Insert. 9 might exhibit 30% relative binding, Insert. 10 might exhibit 15% relative binding, Insert. 11 might exhibit 0% relative binding, Insert. 12 might exhibit 40% relative binding, and Inserts. 13 and 14 might exhibit between 80% and 100% relative binding. This thus teaches that the residues in Insert. 11 involved in metal ion complexation are necessary for binding, and that metal ion complexation has knocked-out the binding activity. The decreased binding on adjacent metal ion complexation sites is indicative of local conformational change resulting in decreased binding. Similar scenarios may readily be hypothesized for the substitution scheme described.

In general, the method may be employed with any parent polypeptide of at least about five amino acid residues, and preferably about eight amino acid residues. The maximum number of residues is limited only by constraints relating to peptide synthesis; in general, the method is well adapted for any parent polypeptide with up to about twenty amino acid residues, though it can be used for longer parent polypeptides, and may be readily employed with any parent polypeptide with between about five and fifteen amino acid residues.

During synthesis the —SH group of Z of the formula $R_1$—Z—$R_2$ may be protected using an orthogonal protecting agent as set forth below. The resulting orthogonally-protected Cys-containing peptide is then deprotected, and subsequently complexed with a metal ion, such as a rhenium ion, thereby forming a metallopeptide, using in the case of a rhenium ion a suitable pre-formed metal-oxo transfer agent, such as $Re(O)Cl_3(PPh_3)_2$. Through use of suitable assays or tests, such as competitive inhibition assays, the binding of each of the resulting metallopeptides is compared against the parent polypeptide, and those metallopeptides with decreased binding are identified as involving a structure about the metal ion complex which "knocksout" the inherent binding site.

By means of the methods and teachings presented herein, any biologically active sequence of two or more amino acid residues which exhibit binding to a receptor found on cells, tissues, organs and other biological materials, may be identified. The term "receptor" is intended to include both acceptors and receptors. The receptor may be a biological receptor. The sequence may transmit a signal to the cells, tissues or other materials associated with the biological receptor after binding, but such is not required. Examples include, but are not limited to, sequences within parent polypeptides specific for hormone receptors, neurotransmitter receptors, cell surface receptors, enzyme receptors and antibody-antigen systems. The parent polypeptide may be either an agonist or antagonist, or a mixed agonist-antagonist. The parent polypeptide may also include any ligand for site-specific RNA or DNA binding, such as sequences that may be employed as mimics of transcription and other gene regulatory proteins. In general, the parent polypeptide will constitute a member of a "specific binding pair," which specific binding pair is made up of at least two different molecules, where one molecule has an area on the surface or in a cavity which specifically binds to a particular spatial and polar organization of the other molecule. Frequently, the members of a specific binding pair are referred to as ligand and receptor or anti-ligand. Examples of specific binding pairs include antibody-antigen pairs, hormone-receptor pairs, peptide-receptor pairs, enzyme-receptor pairs, carbohydrate-protein pairs (glycoproteins), carbohydrate-fat pairs (glycolipids), lectin-carbohydrate pairs and the like.

Through use of suitable screen assays, such as competitive inhibition assays, the binding of each of the resulting metallopeptides is compared against the parent polypeptide, and those with decreased or eliminated binding are identified as involving a metal ion-induced secondary structural motif about the sequence necessary for binding of the parent polypeptide. In this way the specific sequence necessary for biological activity in the parent polypeptide, given the peptide or protein folding conformation implicit in such parent polypeptide, is identified. Once one or more metallopeptides with decreased or eliminated binding are identified, amino acid residues on either the amino or carbonyl ends may be added, subtracted, and the like, side chains modified, and similar changes made to obtain a metallopeptide which further elucidates both the sequence and the secondary structure of the parent polypeptide necessary for biological activity such as binding.

In the event that the parent polypeptide contains one or more endogenous Cys residues, it is possible to protect the intrinsic Cys residues with a non-orthogonal —SH protecting agent, to protect the introduced $N_1S_1$ residue with an orthogonal —SH protecting agent, to thereafter selectively deprotect the orthogonal —SH protecting agent, to then complex the deprotected $N_1S_1$ residue with a metal ion, and thereafter to deprotect the Cys residue with the non-orthogonal —SH protecting agent. Examples of common non-orthogonal —SH protecting groups include, but are not limited to, trityl, benzyl, p-methoxy benzyl, and $^t$Bu.

While the primary structure of the parent polypeptide is known, neither the specific residues involved in binding to the receptor, nor the secondary structure involved in such binding to the receptor is known. Thus definition of the pharmacophore cannot be derived solely from knowledge of the primary structure of the parent polypeptide. Knowledge of the pharmacophore may, for example, permit design and construction of any of a wide variety of small molecules, including peptidomimetics and non-peptide small molecules, which bind to the receptor, optionally acting as either an agonist or antagonist. Based on the primary structure of the known parent polypeptide, a series of metallopeptides is constructed as set forth above. Once the specific residues involved in binding to the receptor are identified by the knockout means set forth herein, the secondary structure can be elucidated by any of a variety of means. In one embodiment, the secondary structure is elucidated as set forth in PCT/US01/50075. For example, much smaller sequences, on the order of three to six residues, may be employed. The secondary structure may be modified by employing different turn structures resulting from different $N_1S_1$ residues (e.g., substituting a D-Cys for an L-Cys). A selected metallopeptide may be optimized as desired, such as by determining the fewest residues yielding acceptable binding, for example such that in the formula $R_1$-Cys-$R_2$, $R_1$ and $R_2$ together constitute no more than three, and optionally preferably only two, residues. Similarly, modifications to optimize the selected metallopeptide may optionally be made with respect to side chains, such that the resulting metallopeptide has desired hydrogen bond donors and acceptors, charged centers, aromatic ring centers, hydrophobic centers and the like, thereby providing optimal binding to the receptor. When a metallopeptide is selected that provides optimal binding to the desired receptor compared to the parent polypeptide, as determined by the methods of this invention, then the metallopeptide so selected may be modeled as set forth in PCT/US01/50075.

The choice of metal ion partially determines the structure of the resulting turning structure. For example, use of a Re ion results in a square pyramidal coordination geometry. Tc (which has substantially similar coordination requirements and chemistries and generally may be substituted for Re in any example herein) similarly results in a square pyramidal coordination geometry. Use of other metal ions, such as Cu, Ni or Zn, results in square planar coordination geometries. Thus while the atomic radius of Re is on the order of 1.37 Å and that of Cu is smaller, on the order of 1.28 Å, the resulting dimensions of the metal coordination group is determined, in large part, by the coordination geometry, and not just by the atomic radius of the metal ion. With metal ions such as Cu, Ni or Zn employing square planar coordination tetradentate geometries, the metal ion and each of the four coordinating atoms (such as S, N or O) are co-planar. However, when employing metal ions such as Re or Tc (which result in square pyramidal coordination tetradentate geometries), the four coordinating atoms (such as S, N or O) are co-planar, but the metal ion is, in the case of Re, about 0.65 Å removed from the plane of the coordinating atoms.

In this invention any of a wide range of metal ions may be employed, but Re and Tc are particularly preferred. Both metals form similar complexes with Cys-containing peptides yielding similar square pyramidal complexes. Re-complexed peptides, however, are chemically more stable than the corresponding Tc-containing peptides. The square planar complexes of Zn and Cu, with the metal ion as well as the four coordinating atoms of the peptide all in one plane, results in a near identical complexation geometry as is obtained with Tc or Re, where the metal ion is projected upwards from the plane of four coordinating atoms of the peptide, notwithstanding the differences in the atomic radius of the metal ions. The net result are metallopeptides that each afford topographic similarities, whether for example Re, Tc, Zn or Cu is employed. The Re-complexed metallopeptides, however, are unique in that the metallopeptides are air and moisture stable, without any need for special or exotic excipients or protecting agents. The Re-complexes can routinely be isolated as solid compounds and are stable as solids and in solutions over a wide pH range, thereby facilitating both analytical characterization and, more importantly, use in both in vitro and in vivo biological experiments over a wide range of conditions. Other metal types, such as Zn-complexes and Cu-complexes, are utilized in experiments in a solution form. However, Zn-complexes and Cu-complexes are extremely easy to form, and essentially are formed in the presence of 1 micromolar to 1 millimolar concentration of the metal ion in an appropriately buffered solution.

The Re- and Tc-complexes are metaloxo complexes, generally and in a preferred embodiment in an oxidation state [V]. The metaloxo core M═O in the metallopeptides may give rise to an isomerism in the core structure. The metal-oxo group may be syn or anti with respect to a chiral amino acid side chain. Since the orientation of the oxo group does not alter the topographic surface created by the amino acid side chains, this isomerism has little or no effect on the biological activity of the metallopeptides. That is, the oxo group of a metal ion does not sterically hinder the conformationally constrained amino acid side chain presentations. In fact, the metal ion is situated at a location spatially similar to that where turns are stabilized by a hydrogen bond in natural turn structures; thus the oxo group falls within a space not addressable in natural turn structures. Computer modeling of individual syn- and anti-isomers of metallopeptides have shown that these two structures are completely indistinguishable with respect to each amino acid location, with orientation of the oxo group being the only difference. Thus while FIGS. 1 through 4 depict one possible configuration of the metal-oxo group, the same results are obtained if the metal-oxo group is in a different configuration.

It may be seen that in the practice of the invention a free thiol or sulfhydryl (—SH) group of a residue is utilized for complexation of metal ions. Peptides and other organic molecules with free-SH groups, however, are easily oxidized in air and in solution, and can often form a disulfide-linked dimer. If more than one free —SH group is present in a molecule, oxidation may lead to a complex polymer. In addition, with more than one free —SH group when the metal ion is complexed to the peptide, it is possible to have metal ion complexation at more than one site in the peptide. This results in mixed species of metallopeptides, thereby complicating determination of the specific metallopeptide responsible for binding to a target of interest, as well as determination of the relevant secondary structure. Similarly, if a mixture of different peptides or organic molecules with free —SH groups are prepared, oxidation generally leads to a complex mixture of polymers of unknown composition. This is of serious concern in preparing libraries of metallopeptides or other organic molecules where one or more —SH group is intended for use in metal complexation.

In order to construct metallopeptides of this invention which incorporate an —SH group, and most particularly in order to construct libraries, it is desirable to employ S-protected derivatives. The S-protecting group is chosen such that (a) the synthesis of peptides with the S-protecting group is compatible with methods of solution and solid phase peptide synthesis, so that the S-protecting group is stable during synthetic procedures, and (b) the S-protecting group can be deprotected in situ, without cleavage from the resin in the case of solid phase synthesis, during the metal complexation step. An S-protecting group meeting the forgoing criteria is defined herein as an orthogonal S-protected group (OSPG). Many prior art protecting groups meet at most only one of the two criteria specified above, and thus do not constitute an OSPG as defined herein.

Use of orthogonally S-protected thiol groups permits synthesis of metallo-compounds in a single vessel. A mixture of compounds, each compound containing an OSPG, is used for complexation with a metal ion, and it is only during metal ion complexation that the S-protected group is deprotected, and accordingly polymerization and cross-linking is avoided. This procedure thus provides homogenous libraries of metallopeptides.

One OSPG meeting the criteria specified above, and which can be advantageously used in this invention, employs an $S^tBu$ (S-thio-butyl or S-t-butyl) group to protect the —SH group. The $S^tBu$ group is stable under both the acidic and basic conditions typically employed in peptide synthesis. Further, the $S^tBu$ group may be cleaved by reduction using a suitable phosphine reagent, which reduction step may be employed immediately prior to, or in conjunction with, complexing of a metal ion to the peptide. Such OSPG cleavage does not cleave the peptide from the resin, or otherwise alter the structure of the peptide.

Another OSPG meeting the criteria specified above and suitable for this invention employs an S-Acm (S-acetamidomethyl) group to protect the —SH group. The Acm group is also stable under the acid and base conditions usually employed during peptide synthesis. The S-Acm group may be removed by treatment of S-Acm-protected peptide or peptide resin with mercury (II) acetate or silver (I) tertrafluoroborate, which liberates the thiol peptide in its mercury or silver ion-complexed state. If a mercury or silver ion metallopeptide is desired, the resulting metallopeptide may be kept in solution and employed in assays as described herein. Alternatively, free thiol-containing peptide can be recovered by treating the mercury or silver ion and thiol complexed salts with an excess of a thiol-containing reagent, such as beta-mercaptoethanol or dithiothreitol. The resulting peptide is then used for metal complexation to a metal such as Re or Tc. Alternatively, the mercury or silver ion and thiol complexed peptide may be directly treated with a metal ion complexing reagent, such as an Re complexing reagent, to form a desired metallopeptide, such as an Re metallopeptide.

Other examples of OSPGs for metallopeptides include 4-methoxytrityl (Mmt), 3-nitro-2-pyridinesulfenyl (Npys) and S-sulfonate ($SO_3H$). Mmt is selectively removed upon treatment with 1% TFA in dichloromethane. Npys and S-sulfonate are selectively removed by treatment with a thiol-containing reagent such as beta-mercaptoethanol or dithiothreitol or a phosphine reagent such as tributyl phosphine. The Npys group (R G Simmonds et al: *Int J Peptide Protein Res,* 43:363, 1994) is compatible with Boc chemistry for peptide synthesis and the S-sulfonate (I Maugras et al: *Int J Peptide Protein Res,* 45:152, 1995) is compatible with both Fmoc and Boc chemistries. Similar OSPGs derived from homologous series of S-alkyl, or S-aryl, or S-aralkyl may also be used in this invention. A primary characterization of the OSPG is that its use results in the formation of a disulfide (S—S) bond utilizing one sulfur atom each from the thiol-containing amino acid and the protecting group. In addition, the resulting disulfide bond is cleavable by the use of any of a variety of disulfide cleaving agents, including but not limited to phosphine- and thiol-containing reagents.

The method employing $S^tBu$ protected —SH groups, or other OSPGs, may be employed for the generation of either solid phase or soluble libraries. For solid phase libraries, peptides may be synthesized by use of conventional Fmoc chemistry. In the case of conventional Fmoc chemistry, Fmoc-L-Cys-($S^tBu$) is coupled to an appropriate resin, via one or more intermediate amino acid residues, and additional amino acid residues are thereafter coupled to the L-Cys-($S^tBu$) residue. $S^tBu$ may be employed with either L- or D-Cys, and any of a variety of other amino acid residues, including designer or unnatural amino acid residues and mimics thereof, characterized by an —SH group available for complexation to a metal ion, including, but not limited to, 3-mercapto phenylananine and other related 3-mercapto amino acid residues such as 3-mercapto valine (penicillamine), all of the foregoing of which constitute an $N_1S_1$ residue. In all these cases, S-protection can be by S-$Bu^t$, S-Acm, Mmt, Npys, S-sulfonate and related groups, as described above.

The complexation of metal ions to the peptides is achieved by mixing the peptides with the metal ion. This is conveniently done in solution, with the solution including an appropriate buffer. In one approach the metal ion is, when mixed with the peptide or peptidomimetic constituents, already in the oxidation state most preferred for complexation. Some metal ions are complexed in their most stable oxidation state, such as calcium (II), potassium (I), indium (III), manganese (II), copper (II), zinc (II) and other metals. In other instances, the metal must be reduced to a lower oxidation state in order to be complexed. This is true of ferrous, ferric, stannous, stannic, technetiumoxo[V], pertechnetate, rheniumoxo[V], perrhenate and other similar metal ions. Reduction may be performed prior to mixing with the sequences, simultaneously with mixing with the sequences, or subsequent to mixing with the sequences. Any means of reduction of metal ions to the desired oxidation state known to the art may be employed.

Re and Tc are preferred metal ions to employ, particularly in that the resulting metallopeptides may be purified and removed from solution, such as by lyophilization, and remain stable. Other metallopeptides, as for example metallopeptides utilizing Zn, Cu, Ni, Co, Fe and Mn, are stable in solution, but are prone to oxidation and loss of the metal ion if removed from solution. Thus these metallopeptides must be kept in solution, and optimally at the appropriate pH and with appropriate buffers, at all times, including during conduct of assays and other tests. This imparts some limitations on the utility of these metal ions; however, metallopeptides utilizing metal ions other than Re or Tc may be employed as discussed herein.

Solid phase resin bound peptide or peptidomimetic sequences may be labeled with rhenium ion by treatment with the rhenium transfer agent $ReOCl_3(PPh_3)_2$ in the presence of a base, such as 1,8-diazabicyclo[5,4,0] undec-7-ene (DBU). The sequences may then be cleaved from the resin. Peptide or peptidomimetic sequences in solution may similarly be labeled by treatment with the rhenium transfer agent $ReOCl_3(PPh_3)_2$ in the presence of a base, such as triethyl amine, disopropylethylamine, N-methylmopholine or DBU. Metal complexation in the presence of DBU as a base can conveniently be accomplished at ambient room temperature.

In an alternative method of metal complexation a mild base, such as sodium acetate, can be used. In this case the thiol-containing sequence, either in solution or bound to solid phase, is taken in a suitable solvent, such as dimethylformamide (DMF), dichloromethane (DCM), N-methylpyrrolidinone (NMP), methanol (MeOH) or a mixture thereof, and heated to 60-70° C. with the rhenium transfer agent $ReOCl_3(PPh_3)_2$ in the presence of sodium acetate for 15 minutes. Similarly, other bases such as triethylamine, ammonium hydroxide and so on, may be employed. According to this invention, MeOH is a preferred choice of solvent for rhenium complexation in the case of S-deprotected peptides in solution. The solvent choice for S-deprotected peptides still attached to the solid phase is guided mainly by considerations of superior solvation (swelling) of the solid phase. DMF and NMP may be employed. Various mixtures of these solvents, also in combination with MeOH, and DCM, $CHCl_3$ and so on, may also be employed to yield optimized complexation results.

In one embodiment of this invention, an $S^tBu$ protected peptide is treated in situ with rhenium transfer agent in the presence of DBU and tributylphosphine to effect S-deprotection and rhenium complexation in one vessel. Alternately, complexing of rhenium to the $S^tBu$ protected peptide in the presence of rhenium perrhenate may be accomplished by treatment with $Sn[II]Cl_2$. This reagent effects S-deprotection as well as conversion of the $ReO_4$ state to an ReO state in situ to thereby effect complexation of the rhenium to the S-deprotected peptide. A preferred procedure in this invention is the use of S-$Bu^t$ protected peptide with S-deprotection by treatment with tributylphosphine, and metal complexation of the resulting peptide utilizing $ReOCl_3(PPh_3)_2$ in the presence of DBU at room temperature.

It is possible and contemplated to prepare libraries of peptides of this invention, and to then complex the resulting peptides to a metal ion, such as rhenium, resulting in a metallopeptide. Such a library may be a solid phase library, or may be a solution phase library. A peptide library is first assembled based on the parent polypeptide, as described above, by well-known methods of peptide synthesis. Both solid-phase and soluble libraries can be obtained in this manner. The entire library is then reacted with an appropriate metal-complexing agent to obtain the corresponding metal-coordinated library, comprising a similar class of predetermined structures. For example, to complex a peptide library with rheniumoxo metal ion, the peptide library can be treated with $Re(O)Cl_3(PPh_3)_2$ in the presence of sodium acetate. This procedure results in quantitative complexation of ReO with the peptide. In order to complex Zn, Ni, Co, Mn, Fe or Cu ions, the peptide library is treated with chloride or other suitable salts of these metal ions to yield the library of corresponding metal ions. Essentially, a variety of metal ions can be used to construct different metallopeptide libraries. One limiting factor in selection of the appropriate metal ion is the relative stability of a particular metal-peptide complex, related in large part to the metal-peptide complex binding constant or constants. It is well known in the art that some metal-peptide constructs are stable only within specified pH or other special conditions, or are easily oxidized in air. Other peptide-metal ion complexes, such as those with ReO, are stable in pure form and can be isolated and stored under normal storage conditions for a long period of time.

In a preferred embodiment a solid-phase methodology is employed for the synthesis of metallopeptides, in which the metal ion complexation is also achieved while the peptide is on the solid phase. Using Fmoc chemistry a linear peptide is fully assembled on rink amide resin using a $S^tBu$ protected Cys derivative. Following synthesis of the peptide, the $S^tBu$ group is removed by treatment with $Bu_3P$ in DMF. The resulting free —SH containing peptide-resin is treated with the rhenium transfer reagent $ReO[V]Cl_3(PPh_3)_2$ in presence of DBU as base. Complete metal-ion complexation is achieved within 2 hours at room temperature. The resulting metallopeptide resin is washed, dried and then treated with TFA to cleave the metallopeptide from the resin and remove all side chain protecting groups. The metallopeptide is purified by HPLC and characterized by mass spectrometry and amino acid analysis.

The invention is further illustrated by the following non-limiting examples:

Example 1 Alpha-MSH with L-Cys Insertion

The first unnumbered peptide in Table 1 is the parent polypeptide, which is an alpha-MSH analog specific for melanocortin receptors. In particular, it is specific for MC1-R and binds with moderate affinity to MC3-R and MC4-R. It binds very weakly to MC5-R. Peptides were synthesized by conventional solid phase synthetic techniques, complexed with rhenium, separated from solid phase and purified by HPLC. As is well known in the art, Met is not oxidatively stable, and thus during synthesis of these peptides Met was replaced with its oxidatively stable homolog, Nle. The metallopeptides 1-1 through 1-12 have the presumptive metal ion complexation tri-peptide sequence identified in italics. Similarly, the italicized percent inhibition numbers represent metallopeptides wherein the secondary structure of the specific sequence responsible for binding in the parent polypeptide has been presumptively disrupted, as shown by decreased percent inhibition.

The competitive inhibition binding assay was conducted using membranes prepared from hMC3-R, hMC4-R, hMC5-R, and B-16 mouse melanoma cells (containing MC1-R) using 0.4 nM $^{125}$I-NDP-alpha-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the test peptide of this invention complexed to a rhenium metal ion, typically at a 1 μM concentration, for determining its efficacy in inhibiting the binding of $^{125}$I-NDP-alpha-MSH to its receptor. Non-specific binding was measured by complete inhibition of binding of $^{125}$I-NDP-alpha-MSH in the assay with the presence of 1 μM alpha-MSH. Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM alpha-MSH. The cpm obtained in presence of test compounds were normalized with respect to 100% specific binding to determine the percent inhibition of $^{125}$I-NDP-alpha MSH binding. Each assay was conducted in triplicate and the actual mean valves are described.

TABLE 1

| | | % Inhibition at 1 μM at Melanocortin Receptor | | | |
|---|---|---|---|---|---|
| No. | Sequence Re-Peptide | 1 | 3 | 4 | 5 |
| Parent | Ac-Ser-Tyr-Ser-Met-Glu-His-Phe-Arg-Trp-Gly-Lys-Pro-Val-$NH_2$ (SEQ ID NO:1)* | 99 | 64 | 69 | 22 |
| 1-1 | Ac-Ser-Tyr-Ser-Nle-Glu-His-Phe-Arg-Trp-Gly-Lys-Gly-Val-Cys-$NH_2$ (SEQ ID NO:2) | 95 | 48 | 63 | 68 |
| 1-2 | Ac-Ser-Tyr-Ser-Nle-Glu-His-Phe-Arg-Trp-Gly-Lys-Gly-Cys-Val-$NH_2$ (SEQ ID NO:3) | 87 | 6 | 0 | 37 |
| 1-3 | Ac-Ser-Tyr-Ser-Nle-Glu-His-Phe-Arg-Trp-Gly-Lys-Cys-Pro-Val-$NH_2$ (SEQ ID NO:4) | 87 | 0 | 0 | 12 |
| 1-4 | Ac-Ser-Tyr-Ser-Nle-Glu-His-Phe-Arg-Trp-Gly-Cys-Lys-Pro-Val-$NH_2$ (SEQ ID NO:5) | 72 | 0 | 0 | 6 |
| 1-5 | Ac-Ser-Tyr-Ser-Nle-Glu-His-Phe-Arg-Trp-Cys-Gly-Lys-Pro-Val-$NH_2$ (SEQ ID NO:6) | 57 | 0 | 0 | 0 |

TABLE 1-continued

| | | % Inhibition at 1 μM at Melanocortin Receptor | | | |
|---|---|---|---|---|---|
| No. | Sequence Re-Peptide | 1 | 3 | 4 | 5 |
| 1-6 | Ac-Ser-Tyr-Ser-Nle-Glu-His-Phe-Arg-Cys-Trp-Gly-Lys-Pro-Val-$NH_2$ (SEQ ID NO:7) | 29 | 0 | 0 | 0 |
| 1-7 | Ac-Ser-Tyr-Ser-Nle-Glu-His-Phe-Cys-Arg-Trp-Gly-Lys-Pro-Val-$NH_2$ (SEQ ID NO:8) | 68 | 0 | 0 | 0 |
| 1-8 | Ac-Ser-Tyr-Ser-Nle-Glu-His-Cys-Phe-Arg-Trp-Gly-Lys-Pro-Val-$NH_2$ (SEQ ID NO:9) | 42 | 0 | 0 | 1 |
| 1-9 | Ac-Ser-Tyr-Ser-Nle-Glu-Cys-His-Phe-Arg-Trp-Gly-Lys-Pro-Val-$NH_2$ (SEQ ID NO:10) | 74 | 0 | 3 | 6 |
| 1-10 | Ac-Ser-Tyr-Ser-Nle-Cys-Glu-His-Phe-Arg-Trp-Gly-Lys-Pro-Val-$NH_2$ (SEQ ID NO:11) | 72 | 0 | 7 | 5 |
| 1-11 | Ac-Ser-Tyr-Ser-Cys-Nle-Glu-His-Phe-Arg-Trp-Gly-Lys-Pro-Val-$NH_2$ (SEQ ID NO:12) | 95 | 18 | 21 | 6 |
| 1-12 | Ac-Ser-Tyr-Cys-Ser-Nle-Glu-His-Phe-Arg-Trp-Gly-Lys-Pro-Val-$NH_2$ (SEQ ID NO:13) | 96 | 15 | 26 | 19 |

*Not complexed to Re metal ion.

The recognized bioactive sequence in alpha-MSH, or message segment, is a tetrapeptide, His-Phe-Arg-Trp (SEQ ID NO:63), that exist as a reverse turn. Within the reverse turn, the His, Phe, and Trp residues have been postulated to form a hydrophobic receptor binding surface. Since the parent peptide is specific for MC1-R, it can been observed from MC1-R data for metallopeptides 1-4 through 1-8 that a general decrease in affinity is associated when metal ion complexes any part of the His-Phe-Arg-Trp (SEQ ID NO:63) sequence. Additionally, placement of metal ion complexation site adjacent to this sequence further resulted in a small but measurable decrease in affinity. Since the parent peptide has weak binding to MC3-R, MC3-R and MC3-R, there was a complete loss of activity seen when metal complexation site was either within or adjacent to the His-Phe-Arg-Trp (SEQ ID NO:63) messenger sequence.

Example 2 Alpha-MSH with D-Cys Insertion

The first unnumbered peptide in Table 2 is the parent polypeptide, which is the alpha-MSH analog specific for melanocortin receptors of Example 1. The methods and assays set forth in Example 1 were followed. The metallopeptides 2-1 through 2-12 have the presumptive metal ion complexation tri-peptide sequence identified in italics. Similarly, the italicized percent inhibition numbers represent metallopeptides wherein the relevant secondary structure in the parent polypeptide has been presumptively disrupted.

TABLE 2

| | | % Inhibition at 1 μM at Melanocortin Receptor | | | |
|---|---|---|---|---|---|
| No. | Sequence Re-Peptide | 1 | 3 | 4 | 5 |
| Parent | Ac-Ser-Tyr-Ser-Met-Glu-His-Phe-Arg-Trp-Gly-Lys-Pro-Val-$NH_2$ (SEQ ID NO:1)* | 99 | 64 | 69 | 22 |
| 2-1 | Ac-Ser-Tyr-Ser-Nle-Glu-His-Phe-Arg-Trp-Gly-Lys-Gly-Val-D-Cys-$NH_2$ | 97 | 72 | 46 | 53 |
| 2-2 | Ac-Ser-Tyr-Ser-Nle-Glu-His-Phe-Arg-Trp-Gly-Lys-Gly-D-Cys-Val-$NH_2$ | 93 | 26 | 28 | 32 |
| 2-3 | Ac-Ser-Tyr-Ser-Nle-Glu-His-Phe-Arg-Trp-Gly-Lys-D-Cys-Pro-Val-$NH_2$ | 91 | 41 | 25 | 38 |

TABLE 2-continued

| No. | Sequence Re-Peptide | % Inhibition at 1 μM at Melanocortin Receptor 1 | 3 | 4 | 5 |
|---|---|---|---|---|---|
| 2-4 | Ac-Ser-Tyr-Ser-Nle-Glu-His-Phe-Arg-Trp-Gly-D-Cys-Lys-Pro-Val-$NH_2$ | 91 | 27 | 40 | 21 |
| 2-5 | Ac-Ser-Tyr-Ser-Nle-Glu-His-Phe-Arg-Trp-D-Cys-Gly-Lys-Pro-Val-$NH_2$ | 43 | 0 | 4 | 0 |
| 2-6 | Ac-Ser-Tyr-Ser-Nle-Glu-His-Phe-Arg-D-Cys-Trp-Gly-Lys-Pro-Val-$NH_2$ | 46 | 2 | 6 | 6 |
| 2-7 | Ac-Ser-Tyr-Ser-Nle-Glu-His-Phe-D-Cys-Arg-Trp-Gly-Lys-Pro-Val-$NH_2$ | 54 | 0 | 6 | 0 |
| 2-8 | Ac-Ser-Tyr-Ser-Nle-Glu-His-D-Cys-Phe-Arg-Trp-Gly-Lys-Pro-Val-$NH_2$ | 69 | 0 | 25 | 29 |
| 2-9 | Ac-Ser-Tyr-Ser-Nle-Glu-D-Cys-His-Phe-Arg-Trp-Gly-Lys-Pro-Val-$NH_2$ | 92 | 13 | 35 | 2 |
| 2-10 | Ac-Ser-Tyr-Ser-Nle-D-Cys-Glu-His-Phe-Arg-Trp-Gly-Lys-Pro-Val-$NH_2$ | 65 | 0 | 18 | 0 |
| 2-11 | Ac-Ser-Tyr-Ser-D-Cys-Nle-Glu-His-Phe-Arg-Trp-Gly-Lys-Pro-Val-$NH_2$ | 95 | 5 | 37 | 0 |
| 2-12 | Ac-Ser-Tyr-D-Cys-Ser-Nle-Glu-His-Phe-Arg-Trp-Gly-Lys-Pro-Val-$NH_2$ | 97 | 21 | 47 | 17 |

*Not complexed to Re metal ion.

As in Example 1, the parent molecule is a specific ligand for MC1-R and exhibits only moderate to low binding to MC3-R, MC4-R, and MC5-R. Therefore the effects of this study are more pronounced for MC1-R. It can be observed from Table 2 that the consecutive series of metallopeptides 2-5 through 2-8 displayed significant loss of binding to MC1-R, presumptively due to placement of the metal ion complexation within the His-Phe-Arg-Trp (SEQ ID NO:63) messenger sequence of the parent peptide. Although the parent peptide binds to MC3-R, MC4-R, and MC5-R with moderate to low affinity, a similar knockout of receptor binding affinity can be observed for the same consecutive series of metallopeptides 2-5 through 2-8 with respect to MC3-R, MC4-R, and MC5-R, within experimental limits of measurement of low affinities.

Example 3 [$Nle^3$, D-$Phe^6$]-Gamma-MSH L-Cys Insertion

The first unnumbered peptide in Table 3 is the parent polypeptide, which is a $Nle^3$, D-$Phe^6$ substituted gamma-MSH analog specific for melanocortin receptors. The methods and assays set forth in Example 1 were followed. The metallopeptides have the presumptive metal ion complexation tri-peptide sequence identified in italics, with L-Cys inserted. Similarly, the italicized percent inhibition numbers represent compounds wherein the relevant secondary structure in the parent polypeptide has been presumptively disrupted.

TABLE 3

| No. | Sequence Re-Peptide | % Inhibition at 1 μM at Melanocortin Receptor 1 | 3 | 4 | 5 |
|---|---|---|---|---|---|
| | Tyr-Val-Nle-Gly-His-D-Phe-Arg-Trp-Asp-Arg-Phe-$NH_2$* | 99 | 100 | 99 | 100 |
| 3-1 | Tyr-Val-Nle-Gly-His-D-Phe-Arg-Trp-Asp-Arg-Phe-Cys-$NH_2$ | 95 | 96 | 98 | 102 |
| 3-2 | Tyr-Val-Nle-Gly-His-D-Phe-Arg-Trp-Asp-Arg-Cys-Phe-$NH_2$ | 99 | 91 | 89 | 100 |
| 3-3 | Tyr-Val-Nle-Gly-His-D-Phe-Arg-Trp-Asp-Cys-Arg-Phe-$NH_2$ | 99 | 95 | 99 | 99 |
| 3-4 | Tyr-Val-Nle-Gly-His-D-Phe-Arg-Trp-Cys-Asp-Arg-Phe-$NH_2$ | 98 | 88 | 94 | 100 |
| 3-5 | Tyr-Val-Nle-Gly-His-D-Phe-Arg-Cys-Trp-Asp-Arg-Phe-$NH_2$ | 83 | 45 | 33 | 81 |
| 3-6 | Tyr-Val-Nle-Gly-His-D-Phe-Cys-Arg-Trp-Asp-Arg-Phe-$NH_2$ | 52 | 20 | 31 | 31 |
| 3-7 | Tyr-Val-Nle-Gly-His-Cys-D-Phe-Arg-Trp-Asp-Arg-Phe-$NH_2$ | 39 | 50 | 28 | 56 |
| 3-8 | Tyr-Val-Nle-Gly-His-Cys-D-Phe-Arg-Trp-Asp-Arg-Phe-$NH_2$ | 86 | 60 | 55 | 84 |
| 3-9 | Tyr-Val-Nle-Gly-Cys-His-D-Phe-Arg-Trp-Asp-Arg-Phe-$NH_2$ | 77 | 69 | 55 | 67 |
| 3-10 | Tyr-Val-Nle-Cys-Gly-His-D-Phe-Arg-Trp-Asp-Arg-Phe-$NH_2$ | 84 | 78 | 80 | 86 |
| 3-11 | Tyr-Val-Cys-Nle-Gly-His-D-Phe-Arg-Trp-Asp-Arg-Phe-$NH_2$ | 95 | 85 | 82 | 92 |

*Not complexed to Re metal ion.

The parent peptide binds to MC1-R, MC3-R, MC4-R, and MC5-R with high affinity. It can be observed form the results in Table 3 that for the set of consecutive metallopeptides 3-5 through 3-7 there is a general decrease in binding affinity towards all the four receptors. This decrease persisted for a few additional metallopeptides in the series (3-8 and 3-9). In all these cases the decrease in affinities of metallopeptides for all four receptors is associated with placement of metal ion complexation within or adjacent to the His-D-Phe-Arg-Trp messenger sequence.

Example 4 [$Nle^3$]-Gamma-MSH L-Cys Insertion

The first unnumbered peptide in Table 4 is the parent polypeptide, which is a $Nle^3$ substituted gamma-MSH analog specific for melanocortin receptors. The methods and assays set forth in Example 1 were followed. The metallopeptides have the presumptive metal ion complexation tri-peptide sequence identified in italics, with L-Cys inserted. Similarly, the italicized percent inhibition numbers represent metallopeptides wherein the relevant secondary structure in the parent polypeptide has been presumptively disrupted.

TABLE 4

| No. | Sequence Re-Peptide | % Inhibition at 1 μM at Melanocortin Receptor 1 | 3 | 4 | 5 |
|---|---|---|---|---|---|
| Parent | Tyr-Val-Nle-Gly-His-Phe-Arg-Trp-Asp-Arg-Phe-$NH_2$ (SEQ ID NO:14)* | 83 | 85 | 58 | 43 |
| 4-1 | Tyr-Val-Nle-Gly-His-Phe-Arg-Trp-Asp-Arg-Phe-Cys-$NH_2$ (SEQ ID NO:15) | 56 | 69 | 36 | 41 |
| 4-2 | Tyr-Val-Nle-Gly-His-Phe-Arg-Trp-Asp-Arg-Cys-Phe-$NH_2$ (SEQ ID NO:16) | 75 | 49 | 23 | 51 |
| 4-3 | Tyr-Val-Nle-Gly-His-Phe-Arg-Trp-Asp-Cys-Arg-Phe-$NH_2$ (SEQ ID NO:17) | 44 | 18 | 23 | 65 |
| 4-4 | Tyr-Val-Nle-Gly-His-Phe-Arg-Trp-Cys-Asp-Arg-Phe-$NH_2$ (SEQ ID NO:18) | 52 | 20 | 39 | 47 |

TABLE 4-continued

| | | % Inhibition at 1 μM at Melanocortin Receptor | | | |
|---|---|---|---|---|---|
| No. | Sequence Re-Peptide | 1 | 3 | 4 | 5 |
| 4-5 | Tyr-Val-Nle-Gly-His-Phe-Arg-Cys-Trp-Asp-Arg-Phe-$NH_2$ (SEQ ID NO:19) | 89 | 87 | 74 | 68 |
| 4-6 | Tyr-Val-Nle-Gly-His-Phe-Cys-Arg-Trp-Asp-Arg-Phe-$NH_2$ (SEQ ID NO:20) | −8 | 5 | −2 | 24 |
| 4-7 | Tyr-Val-Nle-Gly-His-Cys-Phe-Arg-Trp-Asp-Arg-Phe-$NH_2$ (SEQ ID NO:21) | −4 | 17 | 4 | 15 |
| 4-8 | Tyr-Val-Nle-Gly-Cys-His-Phe-Arg-Trp-Asp-Arg-Phe-$NH_2$ (SEQ ID NO:22) | 13 | 33 | −1 | 45 |
| 4-9 | Tyr-Val-Nle-Cys-Gly-His-Phe-Arg-Trp-Asp-Arg-Phe-$NH_2$ (SEQ ID NO:23) | 1 | 19 | 4 | 43 |
| 4-10 | Tyr-Val-Cys-Nle-Gly-His-Phe-Arg-Trp-Asp-Arg-Phe-$NH_2$ (SEQ ID NO:24) | 28 | 10 | 2 | 17 |

*Not complexed to Re metal ion.

[$Nle^3$]-Gamma-MSH is not as potent a ligand for various melanocortin receptors as [$Nle^3$, D-$Phe^6$]-Gamma-MSH described in Example 3. It has high affinity for MC1-R and MC3-R and moderate affinity for MC4-R and MC5-R. As is shown from the data presented in Table 4, metallopeptides 4-5 with a Phe-Arg-Cys metal complexation sequence preserved all receptor binding of the parent polypeptide. This metallopeptide therefore positively demonstrates that the bioactive structure around the His-Phe-Arg-Trp (SEQ ID NO:63) messenger sequence is stabilized for all the receptors by metal ion complexation, as is taught in PCT/US01/50075. However, for MC1-R, MC3-R and MC4-R the consecutive metallopeptides before and after 4-5 are less potent, and thus essentially represent a knockout, presumptively due to biologically unfavorable structures after metal ion complexation. Thus while metallopeptides 4-5 positively elucidates the presumptive pharmacophores, by exhibit binding superior to that of the parent, other metallopeptides, such as 4-6 and 4-7, demonstrate that the structurally changes induced by sequential placement of the Cys residue results in decreased binding.

Example 5 [$Nle^3$, D-$Phe^6$]-Gamma-MSH L-Cys Substitution

The first unnumbered peptide in Table 5 is the parent polypeptide, which is a gamma-MSH analog specific for melanocortin receptors. The methods and assays set forth in Example 1 were followed. The metallopeptides have the presumptive metal ion complexation tri-peptide sequence identified in italics with L-Cys insertion. Similarly, the italicized percent inhibition numbers represent metallopeptides wherein the relevant secondary structure in the parent polypeptide has been presumptively disrupted.

TABLE 5

| | | % Inhibition at 1 μM at Melanocortin Receptor | | | |
|---|---|---|---|---|---|
| No. | Sequence Re-Peptide | 1 | 3 | 4 | 5 |
| Parent | Tyr-Val-Nle-Gly-His-D-Phe-Arg-Trp-Asp-Arg-Phe-$NH_2$* | 99 | 100 | 99 | 100 |
| 5-1 | Tyr-Val-Nle-Gly-His-D-Phe-Arg-Trp-Asp-Arg-Cys-$NH_2$ | 101 | 92 | 95 | 98 |
| 5-2 | Tyr-Val-Nle-Gly-His-D-Phe-Arg-Trp-Asp-Cys-Phe-$NH_2$ | 95 | 39 | 58 | 61 |
| 5-3 | Tyr-Val-Nle-Gly-His-D-Phe-Arg-Trp-Cys-Arg-Phe-$NH_2$ | 100 | 93 | 97 | 100 |
| 5-4 | Tyr-Val-Nle-Gly-His-D-Phe-Arg-Cys-Asp-Arg-Phe-$NH_2$ | 86 | 11 | 18 | 58 |
| 5-5 | Tyr-Val-Nle-Gly-His-D-Phe-Cys-Trp-Asp-Arg-Phe-$NH_2$ | 67 | 15 | 26 | 28 |
| 5-6 | Tyr-Val-Nle-Gly-His-Cys-Arg-Trp-Asp-Arg-Phe-$NH_2$ (SEQ ID NO:65) | 74 | 26 | 4 | 21 |
| 5-7 | Tyr-Val-Nle-Gly-Cys-D-Phe-Arg-Trp-Asp-Arg-Phe-$NH_2$ | 89 | 70 | 69 | 88 |
| 5-8 | Tyr-Val-Nle-Cys-His-D-Phe-Arg-Trp-Asp-Arg-Phe-$NH_2$ | 95 | 89 | 86 | 98 |
| 5-9 | Tyr-Val-Cys-Gly-His-D-Phe-Arg-Trp-Asp-Arg-Phe-$NH_2$ | 89 | 53 | 66 | 53 |

*Not complexed to Re metal ion.

The parent peptide binds to MC1-R, MC3-R, MC4-R and MC5-R with high affinity. It can be observed form the results in Table 5 that for the consecutive metallopeptides 5-4 through 5-6 there is a general decrease in binding affinity with all the four receptors. In all these cases the decrease in affinities of metallopeptides for all the four receptors is associated with placement of metal ion complexation, by substitution, within the His-D-Phe-Arg-Trp messenger sequence. Thus disruption of the His-D-Phe-Arg-Trp sequence demonstrates this sequence as defining the critical pharmacophores for binding.

Example 6 Bombesin with L-Cys Insertion

Here and in the following examples bombesin or bombesin-like peptides were employed. The function of bombesin peptides, and potential parent polypeptides, are disclosed in the scientific literature, including Leban J J et al: *Proc Natl Acad Sci USA* 90:1922-1925, 1993; Hampton L L et al: *Proc Natl Acad Sci USA* 95:3188-3192, 1998; and Yamada K, Wada E and Wada K: *Ann Med* 32:519-529, 2000, all incorporated here by reference.

Rat brain membranes were utilized as the source of bombesin receptor. The competitive binding assay was performed using a procedure as described by Moody T W, Perk C B, Rivier J, Brown, M R. (*Proc Natl Acad Sci USA.* 75:5372-5376, 1985) and adapted to a 96 well format. An aliquot of membranes taken in assay buffer (50 mM Tris and HCl, pH 7.4 containing 1 mg/mL BSA and 2 μg/mL bacitracin) was incubated with 0.01 nM of $^{125}$I-Bombesin with or without varying concentrations of the test compound for 60 min at 4° C. The incubation was terminated by rapid filtration of the assay mixture, followed by washing the filters with ice-cold buffer. The filters were dried and counted in a gamma counter for retained radioactivity. Non-specific binding was measured by including 1 μM Bombesin in the assay tube. The assay was performed in triplicate and results calculated to determine percentage inhibition of the $^{125}$I-Bombesin binding to its receptors by a test compound. The parent polypeptide is shown in Table 6, with metallopeptides having Cys inserted as shown.

TABLE 6

| No. | Sequence Re-Peptide | % Inhibition |
|---|---|---|
| Parent | Pyr-Gln-Arg-Leu-Gly-Asn-Gln-Trp-Ala-Val-Gly-His-Leu-Met-$NH_2$ (SEQ ID NO:25)* | 106 |
| 6-1 | Pyr-Gln-Arg-Leu-Gly-Asn-Gln-Trp-Ala-Val-Gly-His-Leu-Nle-Cys-$NH_2$ (SEQ ID NO:26) | 82 |
| 6-2 | Pyr-Gln-Arg-Leu-Gly-Asn-Gln-Trp-Ala-Val-Gly-His-Leu-Cys-Nle-$NH_2$ (SEQ ID NO:27) | 91 |
| 6-3 | Pyr-Gln-Arg-Leu-Gly-Asn-Gln-Trp-Ala-Val-Gly-His-Cys-Leu-Nle-$NH_2$ (SEQ ID NO:28) | 71 |
| 6-4 | Pyr-Gln-Arg-Leu-Gly-Asn-Gln-Trp-Ala-Val-Gly-Cys-His-Leu-Nle-$NH_2$ (SEQ ID NO:29) | 70 |
| 6-5 | Pyr-Gln-Arg-Leu-Gly-Asn-Gln-Trp-Ala-Val-Cys-Gly-His-Leu-Nle-$NH_2$ (SEQ ID NO:30) | 67 |
| 6-6 | Pyr-Gln-Arg-Leu-Gly-Asn-Gln-Trp-Ala-Cys-Val-Gly-His-Leu-Nle-$NH_2$ (SEQ ID NO:31) | 83 |
| 6-7 | Pyr-Gln-Arg-Leu-Gly-Asn-Gln-Trp-Cys-Ala-Val-Gly-His-Leu-Nle-$NH_2$ (SEQ ID NO:32) | 62 |
| 6-8 | Pyr-Gln-Arg-Leu-Gly-Asn-Gln-Cys-Trp-Ala-Val-Gly-His-Leu-Nle-$NH_2$ (SEQ ID NO:33) | 75 |
| 6-9 | Pyr-Gln-Arg-Leu-Gly-Asn-Cys-Gln-Trp-Ala-Val-Gly-His-Leu-Nle-$NH_2$ (SEQ ID NO:34) | 91 |
| 6-10 | Pyr-Gln-Arg-Leu-Gly-Cys-Asn-Gln-Trp-Ala-Val-Gly-His-Leu-Nle-$NH_2$ (SEQ ID NO:35) | 93 |
| 6-11 | Pyr-Gln-Arg-Leu-Cys-Gly-Asn-Gln-Trp-Ala-Val-Gly-His-Leu-Nle-$NH_2$ (SEQ ID NO:36) | N.D. |
| 6-12 | Pyr-Gln-Arg-Cys-Leu-Gly-Asn-Gln-Trp-Ala-Val-Gly-His-Leu-Nle-$NH_2$ (SEQ ID NO:37) | 97 |
| 6-13 | Ac-Ala-Gln-Cys-Arg-Leu-Gly-Asn-Gln-Trp-Ala-Val-Gly-His-Leu-Nle-$NH_2$ (SEQ ID NO:38) | 99 |

(N.D. indicates "not determined.")
*Not complexed to Re metal ion.

The parent peptide is a natural bombesin molecule isolated from amphibian skin (Anastasi A et al: *Experinetia* 27:166-167, 1971) wherein Met has been replaced with Nle. It may be seen that a significant decrease is seen in Table 6 in consecutive metallopeptides 6-3 to 6-8, corresponding to metal ion complexation within $Asn^6$ to $His^{12}$ of the parent polypeptide. This peptide segment therefore contains key pharmacophore elements that are crucial for biological activity. Example 7 further elucidates identification of certain key features within this segment.

Example 7 Bombesin with L-Cys Substitution

Using the parent polypeptide and methods of Example 6, a second series of metallopeptides were constructed and tested using L-Cys substitution, as shown in Table 7. This series shows complete inhibition with Cys substitution of $Trp^8$, localizing key amino acid residues necessary for binding.

TABLE 7

| No. | Sequence Re-Peptide | % Inhibition |
|---|---|---|
| Parent | Pyr-Gln-Arg-Leu-Gly-Asn-Gln-Trp-Ala-Val-Gly-His-Leu-Met-$NH_2$ (SEQ ID NO:25)* | 106 |
| 7-1 | Pyr-Gln-Arg-Leu-Gly-Asn-Gln-Trp-Ala-Val-Gly-His-Leu-Cys-$NH_2$ (SEQ ID NO:40) | 73 |
| 7-2 | Pyr-Gln-Arg-Leu-Gly-Asn-Gln-Trp-Ala-Val-Gly-His-Cys-Nle-$NH_2$ (SEQ ID NO:41) | 66 |
| 7-3 | Pyr-Gln-Arg-Leu-Gly-Asn-Gln-Trp-Ala-Val-Gly-Cys-Leu-Nle-$NH_2$ (SEQ ID NO:42) | 82 |
| 7-4 | Pyr-Gln-Arg-Leu-Gly-Asn-Gln-Trp-Ala-Val-Cys-His-Leu-Nle-$NH_2$ (SEQ ID NO:43) | 81 |
| 7-5 | Pyr-Gln-Arg-Leu-Gly-Asn-Gln-Trp-Ala-Cys-Gly-His-Leu-Nle-$NH_2$ (SEQ ID NO:44) | 61 |
| 7-6 | Pyr-Gln-Arg-Leu-Gly-Asn-Gln-Trp-Cys-Val-Gly-His-Leu-Nle-$NH_2$ (SEQ ID NO:45) | 91 |

TABLE 7-continued

| No. | Sequence Re-Peptide | % Inhibition |
|---|---|---|
| 7-7 | Pyr-Gln-Arg-Leu-Gly-Asn-Gln-Cys-Ala-Val-Gly-His-Leu-Nle-$NH_2$ (SEQ ID NO:46) | −2 |
| 7-8 | Pyr-Gln-Arg-Leu-Gly-Asn-Cys-Trp-Ala-Val-Gly-His-Leu-Nle-$NH_2$ (SEQ ID NO:47) | 84 |
| 7-9 | Pyr-Gln-Arg-Leu-Gly-Cys-Gln-Trp-Ala-Val-Gly-His-Leu-Nle-$NH_2$ (SEQ ID NO:48) | 93 |
| 7-10 | Pyr-Gln-Arg-Leu-Cys-Asn-Gln-Trp-Ala-Val-Gly-His-Leu-Nle-$NH_2$ (SEQ ID NO:49) | N.D. |
| 7-11 | Pyr-Gln-Arg-Cys-Gly-Asn-Gln-Trp-Ala-Val-Gly-His-Leu-Nle-$NH_2$ (SEQ ID NO:50) | 95 |
| 7-12 | Ac-Ala-Gln-Cys-Leu-Gly-Asn-Gln-Trp-Ala-Val-Gly-His-Leu-Nle-$NH_2$ (SEQ ID NO:51) | 96 |

(N.D. indicates "not determined.")
*Not complexed to Re metal ion.

The results from Table 7 are more dramatic in identification of a key structural organization site, as well as a key amino acid critical for activity within the molecule, and in particular within the $Asn^6$ to $His^{12}$ peptide segment identified in Example 6. Complete inactivity of metallopeptide 7-7 demonstrates the critical importance of metal ion complexation around the $Trp^8$ residue. An analysis of receptor binding data of metallopeptides 7-5 through 7-8 in terms of the presence of Trp in metal-ion complexation shows the importance of the Trp residue and its specific location with respect other elements of the biologically relevant groups.

Example 8 Alternative Bombesin with L-Cys Insertion

Using the competitive inhibition methods of Example 6, the parent polypeptide of Table 8 was used to construct the L-Cys insertion metallopeptides shown.

TABLE 8

| No. | Sequence Re-Peptide | % Inhibition |
|---|---|---|
| Parent | D-Phe-Gln-Trp-Ala-Val-Gly-His-Leu-Leu-$NH_2$* | 92 |
| 8-1 | D-Phe-Gln-Trp-Ala-Val-Gly-His-Leu-Leu-Cys-$NH_2$ | 39 |
| 8-2 | D-Phe-Gln-Trp-Ala-Val-Gly-His-Leu-Cys-Leu-$NH_2$ | 75 |
| 8-3 | D-Phe-Gln-Trp-Ala-Val-Gly-His-Cys-Leu-Leu-$NH_2$ | 49 |
| 8-4 | D-Phe-Gln-Trp-Ala-Val-Gly-Cys-His-Leu-Leu-$NH_2$ | 59 |
| 8-5 | D-Phe-Gln-Trp-Ala-Val-Cys-Gly-His-Leu-Leu-$NH_2$ | 70 |
| 8-6 | D-Phe-Gln-Trp-Ala-Cys-Val-Gly-His-Leu-Leu-$NH_2$ | 35 |
| 8-7 | D-Phe-Gln-Trp-Cys-Ala-Val-Gly-His-Leu-Leu-$NH_2$ | 8 |
| 8-8 | D-Phe-Gln-Cys-Trp-Ala-Val-Gly-His-Leu-Leu-$NH_2$ | 62 |

*Not complexed to Re metal ion.

The parent polypeptide is a potent nine amino acid peptide analog of bombesin (Deschodt-Lanckman M. et al: In vitro actions of bombesin-like peptides in amylase secretion, calcium efflux and adenyl cyclase activity in rat pancreas. *J Clin Invest* 58; 891-898, 1976). The data presented in Table 8 shows the least activity for metallopeptides 8-6 and 8-7. Both these compounds include Trp in the metal-ion complexation sequence. These results thus here too identify Trp and the Trp-containing segment of the parent polypeptide as the biologically critical element. This data is in agreement with the results obtained in Example 7.

Example 9 Alternative Bombesin with L-Cys Substitution

An L-Cys substitution scheme was employed, using the parent polypeptide disclosed in Example 8 and the competitive inhibition methods of Example 6.

TABLE 9

| No. | Sequence Re-Peptide | % Inhibition |
|---|---|---|
| Parent | D-Phe-Gln-Trp-Ala-Val-Gly-His-Leu-Leu-$NH_2$* | 92 |
| 9-1 | D-Phe-Gln-Trp-Ala-Val-Gly-His-Leu-Cys-$NH_2$ | 86 |
| 9-2 | D-Phe-Gln-Trp-Ala-Val-Gly-His-Cys-Leu-$NH_2$ | 35 |
| 9-3 | D-Phe-Gln-Trp-Ala-Val-Gly-Cys-Leu-Leu-$NH_2$ | 70 |
| 9-4 | D-Phe-Gln-Trp-Ala-Val-Cys-His-Leu-Leu-$NH_2$ | 75 |
| 9-5 | D-Phe-Gln-Trp-Ala-Cys-Gly-His-Leu-Leu-$NH_2$ | 17 |
| 9-6 | D-Phe-Gln-Trp-Cys-Val-Gly-His-Leu-Leu-$NH_2$ | 43 |
| 9-7 | D-Phe-Gln-Cys-Ala-Val-Gly-His-Leu-Leu-$NH_2$ | 19 |

*Not complexed to Re metal ion.

The data presented in Table 9 shows the least activity for metallopeptides 9-5 and 9-7. The 9-5 and 9-6 metallopeptides include Trp in the metal-ion complexation sequence, while metallopeptide 9-7 has Trp substituted for Cys for metal ion complexation. The results thus here too identify Trp and the Trp-containing segment of the parent polypeptide as the biologically critical element. This data is in agreement with the results obtained in Example 7 and 8.

Example 10 Further Bombesin Evaluation

Based on the metallopeptide 9-4 disclosed in Table 9, and using the methods of Example 6, a series of metallopeptides was constructed by modifying the Cys and its flanking residues sequentially with D-variants as shown, to further elucidate information about the pharmacophore.

TABLE 10

| No. | Sequence Re-Peptide | % Inhibition |
|---|---|---|
| 9-4 | D-Phe-Gln-Trp-Ala-Val-Cys-His-Leu-Leu-$NH_2$ | 75 |
| 10-1 | D-Phe-Gln-Trp-Ala-Val-Cys-D-His-Leu-Leu-$NH_2$ | 10 |
| 10-2 | D-Phe-Gln-Trp-Ala-Val-D-Cys-His-Leu-Leu-$NH_2$ | 64 |
| 10-3 | D-Phe-Gln-Trp-Ala-D-Val-Cys-His-Leu-Leu-$NH_2$ | 7 |
| 10-4 | D-Phe-Gln-Trp-D-Ala-Val-Cys-His-Leu-Leu-$NH_2$ | 2 |
| 10-5 | D-Phe-Gln-D-Trp-Ala-Val-Cys-His-Leu-Leu-$NH_2$ | 6 |

The results shown in Table 10 provide a comprehensive view of the stereochemical relationship between amino acid residues in the biologically critical Trp-Ala-Val-Cys-His (SEQ ID NO:39) segment of metallopeptide 9-4. It is evident from this data that only an all "L" construct affords the correct stereochemical combination.

Example 11 Further Bombesin Evaluation

Using the 9-4 metallopeptide of Table 9, and the methods of Example 6, a series of metallopeptides was constructed modifying the length of metallopeptide 9-4, with truncation at either or both the C- and N-terminus, as shown in Table 11.

TABLE 11

| No. | Sequence Re-Peptide | % Inhibition |
|---|---|---|
| 9-4 | D-Phe-Gln-Trp-Ala-Val-Cys-His-Leu-Leu-$NH_2$ | 75 |
| 11-1 | D-Phe-Gln-Trp-Ala-Val-Cys-His-Leu-$NH_2$ | 98 |
| 11-2 | D-Phe-Gln-Trp-Ala-Val-Cys-His-$NH_2$ | 25 |
| 11-3 | D-Phe-Gln-Trp-Ala-Val-Cys-$NH_2$ | −81 |
| 11-4 | Gln-Trp-Ala-Val-Cys-His-Leu-Leu-$NH_2$ (SEQ ID NO:52) | 25 |
| 11-5 | Trp-Ala-Val-Cys-His-Leu-Leu-$NH_2$ (SEQ ID NO:53) | 18 |
| 11-6 | Ala-Val-Cys-His-Leu-Leu-$NH_2$ (SEQ ID NO:54) | 6 |
| 11-7 | Gln-Trp-Ala-Val-Cys-His-Leu-Leu-$NH_2$ (SEQ ID NO:55) | 5 |
| 11-8 | Trp-Ala-Val-Cys-His-Leu-$NH_2$ (SEQ ID NO:56) | 13 |
| 11-9 | Ala-Val-Cys-His-Leu-$NH_2$ (SEQ ID NO:57) | 7 |
| 11-10 | Gln-Trp-Ala-Val-Cys-His-$NH_2$ (SEQ ID NO:58) | N.D. |
| 11-11 | Trp-Ala-Val-Cys-His-$NH_2$ (SEQ ID NO:59) | −1 |
| 11-12 | Ala-Val-Cys-His-$NH_2$ (SEQ ID NO:60) | 5 |
| 11-13 | Gln-Trp-Ala-Val-Cys-$NH_2$ (SEQ ID NO:61) | −50 |
| 11-14 | Trp-Ala-Val-Cys-$NH_2$ (SEQ ID NO:62) | 8 |
| 11-15 | Ala-Val-Cys-$NH_2$ | 4 |

(N.D. indicates "not determined.")

The results presented in Table 11 show that truncation of the terminal Leu at the C-terminus of metallopeptide 94 enhanced potency, thereby further suggesting optimization of the structure at a site auxiliary to the critical metal-ion complexed site identified in Examples 8 and 9. Surprisingly, in this study metallopeptides 11-3 and 11-13 were found to presumptively displace non-specific excess levels of the radioligand as shown by high negative percent inhibition results. All other truncations led to significantly less active compounds. These results therefore demonstrate the presence of elements auxiliary to the critical peptide segment Gln-Trp-Ala-Val (SEQ ID NO:64) for biological activity of this bombesin analog.

Example 12 Further Bombesin Evaluation

Again using the metallopeptide 9-4 of Table 9, and the methods of Example 6, a series of metallopeptides were constructed with amino acid residue substitution and deletion as shown in Table 12.

TABLE 12

| No. | Sequence Re-Peptide | % Inhibition |
|---|---|---|
| 9-4 | D-Phe-Gln-Trp-Ala-Val-Cys-His-Leu-Leu-$NH_2$ | 75 |
| 12-1 | D-Phe-Gln-Trp-Val-Cys-Gly-His-Leu-Leu-$NH_2$ | 2 |
| 12-2 | D-Phe-Gln-Trp-Ala-Cys-Val-His-Leu-Leu-$NH_2$ | 3 |
| 12-3 | D-Phe-Gln-Trp-Val-Cys-Val-His-Leu-Leu-$NH_2$ | 14 |
| 12-4 | D-Phe-Gln-Trp-Val-Cys-His-Leu-Leu-$NH_2$ | 5 |
| 12-5 | D-Phe-Gln-Trp-Cys-Val-Gly-His-Leu-Leu-$NH_2$ | 43 |
| 12-6 | D-Phe-Gln-Trp-Cys-Val-His-Leu-Leu-$NH_2$ | 10 |

The metallopeptides of Table 12 were varied to determine if each of the Ala, Val and Gly residues in the parent bombesin molecule (see Tables 8 and 9) were critical for activity or were functioning as spacers. The data clearly suggest that substitutions at these amino acids disrupt the stereo-chemical alignments within the Gln-Trp-Ala-Val (SEQ ID NO:64) segment and its relation with C- and N-terminus residues, as further shown in Examples 10 and 11.

The preceding examples can be repeated with similar success by substituting the generically or specifically described reactants and/or operating conditions of this invention for those used in the preceding examples. In specific, while the examples demonstrate utility with a variety of melanocortin and bombesin receptor-specific molecules, the methods in general can be employed with any receptor-specific molecule, and in particular any known molecule which can constitute a "parent polypeptide" as defined herein, and for which at least one binding or functionality assay or test is known or can be developed. Thus parent polypeptides include, without limitation, biologically active peptides, proteins, hormones, neurotransmitters, enzymes, antibodies, fragments or segments of any of the foregoing, and the like. Such parent polypeptides may transmit signals, directly or indirectly, as a result of binding to a receptor, and thus a parent polypeptide may be an agonist, an antagonist, or a mixed agonist-antagonist. Examples of suitable parent polypeptides of the invention include melanocortin-receptor specific peptides, urokinase-type tissue plasminogen activator protein, amyloid beta-protein related peptides, prion disease related peptides, vasopressin peptides, oxytocin peptides, angiotensin peptides, calcitonin, calcitonin gene related peptide, bradykinin, cholecystokinin, urotensin, bombesin, neuromedin B, gastrin releasing peptide, atrial naturetic peptide, somatostatin, opioid peptides, human growth hormone, human prolactin receptor ligands, various interferons such as alpha-interferon, epidermal growth factor, tumor necrosis factor, and various hypotensive peptides, fibrinolytic peptides, chemotactic peptides, growth factor peptides, growth promoter peptides, mitogens, immunomodulators and the like.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of determining the specific residues binding to a target of interest, such residues being within a known parent polypeptide that binds to the target of interest, comprising the steps of:

(a) providing a known parent polypeptide with a known primary structure, such primary structure consisting of n residues where n is 3 to about 20 amino acid residues, which parent polypeptide binds to a target of interest;

(b) constructing a first peptide of the formula $R_1$—Z—$R_2$, wherein $R_1$ comprises from 2 to n residues, such residues being the same as residues in the parent polypeptide and in the same order as residues in the parent polypeptide primary structure, provided that any proline residue in the two residue positions immediately adjacent the amino-terminus side of Z is substituted with glycine, alanine, serine, 2-aminoisobutyric acid (Aib), 1-amino, 1-cyclopentane carboxylic acid, or dehydroalanine, and any cysteine residue in $R_1$ is S-protected or substituted with glycine, alanine, serine, 2-aminoisobutyric acid, 1-amino, 1-cyclopentane carboxylic acid, or dehydroalanine;

Z is an amino acid residue providing both a nitrogen atom (N) and a sulfur atom (S) for metal ion complexation;

$R_2$ comprises from 0 to n−2 residues, such residues being the same as residues in the parent polypeptide and in the same order as residues in the parent polypeptide primary structure, provided that any cysteine residue is S-protected or substituted with glycine, alanine, serine, 2-aminoisobutyric acid, 1-amino, 1-cyclopentane carboxylic acid, or dehydroalanine, and forming with $R_1$ a sequence in the same order as in the parent polypeptide primary structure with Z either inserted between two adjacent residues corresponding to two adjacent residues in such primary structure or substituting for a single residue corresponding to a single residue in such primary structure, and wherein the residues comprising $R_1$—Z—$R_2$ are equal to either n or n+1;

(c) complexing the first peptide of the formula $R_1$—Z—$R_2$ to a rhenium (Re) or technetium (Tc) metal ion, thereby forming a first $R_1$—Z—$R_2$ metallopeptide;

(d) screening the first $R_1$—Z—$R_2$ metallopeptide for binding to the target of interest;

(e) repeating steps (b) through (d), wherein the resulting $R_1$—Z—$R_2$ metallopeptide differs in at least either $R_1$ or $R_2$; and (f) selecting the $R_1$—Z—$R_2$ metallopeptide exhibiting decreased binding to the target of interest as compared to the binding of the parent polypeptide to the target of interest, whereby at least one residue of the sequence binding to the metal ion of such $R_1$—Z—$R_2$ metallopeptide is identified as the specific residues of the parent polypeptide binding to the target of interest.

2. The method of claim 1 wherein Z is an L- or D-3-mercapto amino acid.

3. The method of claim 2 wherein the L- or D-3-mercapto amino acid is L- or D-cysteine, or L- or D-penicillamine, or 3 mercapto phenylalanine.

4. The method of claim 1 wherein the target of interest is a receptor, antibody, toxin, enzyme, hormone, nucleic acid, intracellular protein domain of biological relevance or extracellular protein domain of biological relevance.

5. The method of claim 1 wherein screening for binding to the target of interest comprises competing a known binding partner for binding to the target of interest with the $R_1$—Z—$R_2$ metallopeptide.

6. The method of claim 5 wherein the known binding partner is the parent polypeptide.

7. The method of claim 1 wherein screening for binding to the target of interest comprises a functional assay.

8. The method of claim 1 wherein the target of interest is a biological receptor capable of transmitting a signal, and screening further comprises determining whether the $R_1$—Z—$R_2$ metallopeptide induces decreased transmission of the signal.

9. A method of determining the specific residues binding to a target of interest within a known parent polypeptide that binds to the target of interest, comprising the steps of:

(a) providing a parent polypeptide with a known primary sequence consisting of from three to about twenty amino acid residues;

(b) making a series of peptides, wherein each peptide in the series includes the known primary sequence of the parent polypeptide and a single inserted L- or D-3-mercapto amino acid residue, with the single L- or D-3-mercapto amino acid inserted for each peptide at each position along the primary sequence from the position between the second and third residues from the N-terminus through the C-terminus position;

(c) complexing each peptide in the series with a rhenium or technetium metal ion to form a series of metallopeptides;

(d) determining the binding of each metallopeptide of the series of metallopeptides to the target of interest;

(e) selecting the metallopeptide or metallopeptides of the series exhibiting decreased binding to the target of interest as compared to the binding of the parent polypeptide to the target of interest; and (f) identifying the amino acid residues involved in rhenium or technetium metal ion complexation other than the inserted L- or D-3-mercapto amino acid residue;

whereby at least one of the identified amino acid residues involved in rhenium or technetium metal ion complexation is the specific residues binding to a target of interest within the known parent polypeptide that binds to the target of interest.

10. The method of claim 9, wherein any L- or D-3-mercapto amino acid residue in the series of peptides other than the single inserted L- or D-3-mercapto amino acid residue is modified with a sulfur protecting group, whereby the sulfur therein cannot complex a metal ion.

11. The method of claim 9, wherein any L- or D-3-mercapto amino acid residue in the series of peptides other than the single inserted L- or D-3-mercapto amino acid residue is substituted with glycine, alanine, serine, 2-aminoisobutyric acid, 1-amino, 1-cyclopentane carboxylic acid, or dehydroalanine.

12. The method of claim 9, wherein for any peptide in the series containing a proline residue in either of the two residues on the immediately adjacent N-terminus side of the single inserted L- or D-3-mercapto amino acid residue, the proline residue is substituted with glycine, alanine, serine, 2-aminoisobutyric acid, 1-amino, 1-cyclopentane carboxylic acid, or dehydroalanine.

13. The method of claim 9 wherein the L- or D-3-mercapto amino acid is L- or D-cysteine, or L- or D-penicillamine.

14. The method of claim 9 wherein the target of interest is a receptor, antibody, toxin, enzyme, hormone, nucleic acid, intracellular protein domain of biological relevance or extracellular protein domain of biological relevance.

15. The method of claim 9, wherein determining the binding of each metallopeptide of the series of metallopeptides to the target of interest comprises competing a known binding partner for binding to the target of interest with each metallopeptide.

16. The method of claim 9, wherein determining the binding of each metallopeptide of the series of metallopeptides to the target of interest comprises a functional assay.

17. The method of claim 9, wherein the target of interest is a biological receptor capable of transmitting a signal, and wherein determining the binding of each metallopeptide of the series of metallopeptides to the target of interest comprises determining whether each metallopeptide induces decreased transmission of the signal.

18. A method of determining the specific residues binding to a target of interest within a known parent polypeptide that binds to the target of interest, comprising the steps of:

(a) providing a parent polypeptide with a known primary sequence consisting of from three to about twenty amino acid residues;

(b) making a series of peptides, wherein each peptide in the series includes the known primary sequence of the parent polypeptide with a single substitution, the single substituent consisting of an L- or D-3-mercapto amino acid residue substituted at each position along the primary sequence from the third residue from the N-terminus through the C-terminus residue;

(c) complexing each peptide in the series with a rhenium or technetium metal ion to form a series of metallopeptides;

(d) determining the binding of each metallopeptide of the series of metallopeptides to the target of interest;

(e) selecting the metallopeptide or metallopeptides of the series exhibiting decreased binding to the target of interest as compared to the binding of the parent polypeptide to the target of interest; and (f) identifying the amino acid residues involved in rhenium or technetium metal ion complexation;

whereby at least one of the identified amino acid residues involved in rhenium or technetium metal ion complexation and/or the amino acid residue substituted with an L- or D-3-mercaptoamino acid residue are the specific residues binding to a target of interest within the known parent polypeptide that binds to the target of interest.

19. The method of claim 18, wherein any L- or D-3-mercapto amino acid residue in the series of peptides other than the single substituent L- or D-3-mercapto amino acid residue is modified with a sulfur protecting group, whereby the sulfur therein cannot complex a metal ion.

20. The method of claim 18, wherein any L- or D-3-mercapto amino acid residue in the series of peptides other than the single substituent L- or D-3-mercapto amino acid residue is substituted with glycine, alanine, serine, 2-aminoisobutyric acid, 1-amino, 1-cyclopentane carboxylic acid, or dehydroalanine.

21. The method of claim 18, wherein for any peptide in the series containing a proline residue in either of the two residues on the immediately adjacent N-terminus side of the single substituent L- or D-3-mercapto amino acid residue, the proline residue is substituted with glycine, alanine, serine, 2-aminoisobutyric acid, 1-amino, 1-cyclopentane carboxylic acid, or dehydroalanine.

22. The method of claim 18 wherein the L- or D-3-mercapto amino acid is L- or D-cysteine, or L- or D-penicillamine.

23. The method of claim 18, wherein the target of interest is a receptor, antibody, toxin, enzyme, hormone, nucleic acid, intracellular protein domain of biological relevance or extracellular protein domain of biological relevance.

24. The method of claim 18, wherein determining the binding of each metallopeptide of the series of metallopeptides to the target of interest comprises competing a known binding partner for binding to the target of interest with each metallopeptide.

25. The method of claim 18, wherein determining the binding of each metallopeptide of the series of metallopeptides to the target of interest comprises a functional assay.

26. The method of claim 18, wherein the target of interest is a biological receptor capable of transmitting a signal, and wherein determining the binding of each metallopeptide of the series of metallopeptides to the target of interest comprises determining whether each metallopeptide induces decreased transmission of the signal.

* * * * *

SEQUENCE LISTING

<160> NUMBER OF SEQ ID NOS: 65

<210> SEQ ID NO 1
<211> LENGTH: 13
<212> TYPE: PRT
<213> ORGANISM: Artificial
<220> FEATURE:
<223> OTHER INFORMATION: alpha-MSH analog specific for melanocortin receptors

<400> SEQUENCE: 1

Ser Tyr Ser Met Glu His Phe Arg Trp Gly Lys Pro Val
1 5 10

<210> SEQ ID NO 2
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 2

Ser Tyr Ser Xaa Glu His Phe Arg Trp Gly Lys Gly Val Cys
1 5 10

<210> SEQ ID NO 3
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 3

Ser Tyr Ser Xaa Glu His Phe Arg Trp Gly Lys Gly Cys Val
1 5 10

<210> SEQ ID NO 4
<211> LENGTH: 14

-continued

<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: misc_feature
<222> LOCATION: (4)..(4)
<223> OTHER INFORMATION: Norleucine

<400> SEQUENCE: 4

Ser Tyr Ser Xaa Glu His Phe Arg Trp Gly Lys Cys Pro Val
1 5 10

<210> SEQ ID NO 5
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 5

Ser Tyr Ser Xaa Glu His Phe Arg Trp Gly Cys Lys Pro Val
1 5 10

<210> SEQ ID NO 6
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 6

Ser Tyr Ser Xaa Glu His Phe Arg Trp Cys Gly Lys Pro Val
1 5 10

<210> SEQ ID NO 7
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 7

Ser Tyr Ser Xaa Glu His Phe Arg Cys Trp Gly Lys Pro Val
1 5 10

<210> SEQ ID NO 8
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 8

-continued

Ser Tyr Ser Xaa Glu His Phe Cys Arg Trp Gly Lys Pro Val
1 5 10

<210> SEQ ID NO 9
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: misc_feature
<222> LOCATION: (4)..(4)
<223> OTHER INFORMATION: Xaa can be any naturally occurring amino acid

<400> SEQUENCE: 9

Ser Tyr Ser Xaa Glu His Phe Cys Arg Trp Gly Lys Pro Val
1 5 10

<210> SEQ ID NO 10
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 10

Ser Tyr Ser Xaa Glu Cys His Phe Arg Trp Gly Lys Pro Val
1 5 10

<210> SEQ ID NO 11
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 11

Ser Tyr Ser Xaa Cys Glu His Phe Arg Trp Gly Lys Pro Val
1 5 10

<210> SEQ ID NO 12
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (5)..(5)
<223> OTHER INFORMATION: Norleucine

<400> SEQUENCE: 12

Ser Tyr Ser Cys Xaa Glu His Phe Arg Trp Gly Lys Pro Val
1 5 10

<210> SEQ ID NO 13
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:

-continued

```
<221> NAME/KEY: MISC_FEATURE
<222> LOCATION: (5)..(5)
<223> OTHER INFORMATION: Norleucine

<400> SEQUENCE: 13

Ser Tyr Cys Ser Xaa Glu His Phe Arg Trp Gly Lys Pro Val
1               5                   10


<210> SEQ ID NO 14
<211> LENGTH: 11
<212> TYPE: PRT
<213> ORGANISM: Artificial
<220> FEATURE:
<223> OTHER INFORMATION: Nle-3 substituted gamma-MSH analog for
      melanocortin receptors
<220> FEATURE:
<221> NAME/KEY: MISC_FEATURE
<222> LOCATION: (3)..(3)
<223> OTHER INFORMATION: Norleucine

<400> SEQUENCE: 14

Tyr Val Xaa Gly His Phe Arg Trp Asp Arg Phe
1               5                   10


<210> SEQ ID NO 15
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 15

Tyr Val Xaa Gly His Phe Arg Trp Asp Arg Phe Cys
1               5                   10


<210> SEQ ID NO 16
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 16

Tyr Val Xaa Gly His Phe Arg Trp Asp Arg Cys Phe
1               5                   10


<210> SEQ ID NO 17
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 17

Tyr Val Xaa Gly His Phe Arg Trp Asp Cys Arg Phe
```

-continued

```
1               5                   10


<210> SEQ ID NO 18
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 18

Tyr Val Xaa Gly His Phe Arg Trp Cys Asp Arg Phe
1               5                   10


<210> SEQ ID NO 19
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 19

Tyr Val Xaa Gly His Phe Arg Cys Trp Asp Arg Phe
1               5                   10


<210> SEQ ID NO 20
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 20

Tyr Val Xaa Gly His Phe Cys Arg Trp Asp Arg Phe
1               5                   10


<210> SEQ ID NO 21
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 21

Tyr Val Xaa Gly His Cys Phe Arg Trp Asp Arg Phe
1               5                   10


<210> SEQ ID NO 22
<211> LENGTH: 12
<212> TYPE: PRT
<213> ORGANISM: Artificial
```

-continued

<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 22

Tyr Val Xaa Gly Cys His Phe Arg Trp Asp Arg Phe
1               5                   10

<210> SEQ ID NO 23
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 23

Tyr Val Xaa Cys Gly His Phe Arg Trp Asp Arg Phe
1               5                   10

<210> SEQ ID NO 24
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (4)..(4)
<223> OTHER INFORMATION: Norleucine

<400> SEQUENCE: 24

Tyr Val Cys Xaa Gly His Phe Arg Trp Asp Arg Phe
1               5                   10

<210> SEQ ID NO 25
<211> LENGTH: 14
<212> TYPE: PRT
<213> ORGANISM: Artificial
<220> FEATURE:
<223> OTHER INFORMATION: Bombesin analog derived from amphibian skin
<220> FEATURE:
<221> NAME/KEY: MISC_FEATURE
<222> LOCATION: (1)..(1)
<223> OTHER INFORMATION: Pyroglutamic acid

<400> SEQUENCE: 25

Xaa Gln Arg Leu Gly Asn Gln Trp Ala Val Gly His Leu Met
1               5                   10

<210> SEQ ID NO 26
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE -continued
<222> LOCATION: (14)..(14)
<223> OTHER INFORMATION: Norleucine

<400> SEQUENCE: 26

Xaa Gln Arg Leu Gly Asn Gln Trp Ala Val Gly His Leu Xaa Cys
1 5 10 15

<210> SEQ ID NO 27
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 27

Xaa Gln Arg Leu Gly Asn Gln Trp Ala Val Gly His Leu Cys Xaa
1 5 10 15

<210> SEQ ID NO 28
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 28

Xaa Gln Arg Leu Gly Asn Gln Trp Ala Val Gly His Cys Leu Xaa
1 5 10 15

<210> SEQ ID NO 29
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 29

Xaa Gln Arg Leu Gly Asn Gln Trp Ala Val Gly Cys His Leu Xaa
1 5 10 15

<210> SEQ ID NO 30
<211> LENGTH: 15
<212> TYPE: PRT
<213> ORGANISM: Artificial
<220> FEATURE:
<223> OTHER INFORMATION: metallopeptide derived from bombesin analog
<220> FEATURE:

-continued

<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 30

Xaa Gln Arg Leu Gly Asn Gln Trp Ala Val Cys Gly His Leu Xaa
1 5 10 15

<210> SEQ ID NO 31
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 31

Xaa Gln Arg Leu Gly Asn Gln Trp Ala Cys Val Gly His Leu Xaa
1 5 10 15

<210> SEQ ID NO 32
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 32

Xaa Gln Arg Leu Gly Asn Gln Trp Cys Ala Val Gly His Leu Xaa
1 5 10 15

<210> SEQ ID NO 33
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 33

Xaa Gln Arg Leu Gly Asn Gln Cys Trp Ala Val Gly His Leu Xaa
1 5 10 15

<210> SEQ ID NO 34
<211> LENGTH: 15

-continued

<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 34

Xaa Gln Arg Leu Gly Asn Cys Gln Trp Ala Val Gly His Leu Xaa
1               5                   10                  15

<210> SEQ ID NO 35
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 35

Xaa Gln Arg Leu Gly Cys Asn Gln Trp Ala Val Gly His Leu Xaa
1               5                   10                  15

<210> SEQ ID NO 36
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 36

Xaa Gln Arg Leu Cys Gly Asn Gln Trp Ala Val Gly His Leu Xaa
1               5                   10                  15

<210> SEQ ID NO 37
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 37

Xaa Gln Arg Cys Leu Gly Asn Gln Trp Ala Val Gly His Leu Xaa

-continued 1 5 10 15

<210> SEQ ID NO 38
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (15)..(15)
<223> OTHER INFORMATION: Norleucine
<220> FEATURE:
<221> NAME/KEY: misc_feature
<222> LOCATION: (15)..(15)
<223> OTHER INFORMATION: Norleucine

<400> SEQUENCE: 38

Ala Gln Cys Arg Leu Gly Asn Gln Trp Ala Val Gly His Leu Xaa
1 5 10 15

<210> SEQ ID NO 39
<211> LENGTH: 5
<212> TYPE: PRT
<213> ORGANISM: Artificial
<220> FEATURE:
<223> OTHER INFORMATION: Metallopeptide core sequence derived from bombesin analog

<400> SEQUENCE: 39

Trp Ala Val Cys His
1 5

<210> SEQ ID NO 40
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid

<400> SEQUENCE: 40

Xaa Gln Arg Leu Gly Asn Gln Trp Ala Val Gly His Leu Cys
1 5 10

<210> SEQ ID NO 41
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 41

Xaa Gln Arg Leu Gly Asn Gln Trp Ala Val Gly His Cys Xaa
1 5 10

<210> SEQ ID NO 42
<211> LENGTH: 14
<212> TYPE: PRT

-continued

<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 42

Xaa Gln Arg Leu Gly Asn Gln Trp Ala Val Gly Cys Leu Xaa
1 5 10

<210> SEQ ID NO 43
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 43

Xaa Gln Arg Leu Gly Asn Gln Trp Ala Val Cys His Leu Xaa
1 5 10

<210> SEQ ID NO 44
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 44

Xaa Gln Arg Leu Gly Asn Gln Trp Ala Cys Gly His Leu Xaa
1 5 10

<210> SEQ ID NO 45
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 45

Xaa Gln Arg Leu Gly Asn Gln Trp Cys Val Gly His Leu Xaa
1 5 10

-continued

<210> SEQ ID NO 46
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 46

Xaa Gln Arg Leu Gly Asn Gln Cys Ala Val Gly His Leu Xaa
1               5                   10

<210> SEQ ID NO 47
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 47

Xaa Gln Arg Leu Gly Asn Cys Trp Ala Val Gly His Leu Xaa
1               5                   10

<210> SEQ ID NO 48
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 48

Xaa Gln Arg Leu Gly Cys Gln Trp Ala Val Gly His Leu Xaa
1               5                   10

<210> SEQ ID NO 49
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine -continued

<400> SEQUENCE: 49

Xaa Gln Arg Leu Cys Asn Gln Trp Ala Val Gly His Leu Xaa
1 5 10

<210> SEQ ID NO 50
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 50

Xaa Gln Arg Cys Gly Asn Gln Trp Ala Val Gly His Leu Xaa
1 5 10

<210> SEQ ID NO 51
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (14)..(14)
<223> OTHER INFORMATION: Norleucine

<400> SEQUENCE: 51

Ala Gln Cys Leu Gly Asn Gln Trp Ala Val Gly His Leu Xaa
1 5 10

<210> SEQ ID NO 52
<211> LENGTH: 8
<212> TYPE: PRT
<213> ORGANISM: Artificial
<220> FEATURE:
<223> OTHER INFORMATION: metallopeptide derived from bombesin analog

<400> SEQUENCE: 52

Gln Trp Ala Val Cys His Leu Leu
1 5

<210> SEQ ID NO 53
<211> LENGTH: 7
<212> TYPE: PRT
<213> ORGANISM: Artificial
<220> FEATURE:
<223> OTHER INFORMATION: metallopeptide derived from bombesin analog

<400> SEQUENCE: 53

Trp Ala Val Cys His Leu Leu
1 5

<210> SEQ ID NO 54
<211> LENGTH: 6
<212> TYPE: PRT
<213> ORGANISM: Artificial
<220> FEATURE:
<223> OTHER INFORMATION: metallopeptide derived from bombesin analog

<400> SEQUENCE: 54

-continued

Ala Val Cys His Leu Leu
1 5

<210> SEQ ID NO 55
<211> LENGTH: 7
<212> TYPE: PRT
<213> ORGANISM: Artificial
<220> FEATURE:
<223> OTHER INFORMATION: metallopeptide derived from bombesin analog

<400> SEQUENCE: 55

Gln Trp Ala Val Cys His Leu
1 5

<210> SEQ ID NO 56
<211> LENGTH: 6
<212> TYPE: PRT
<213> ORGANISM: Artificial
<220> FEATURE:
<223> OTHER INFORMATION: metallopeptide derived from bombesin analog

<400> SEQUENCE: 56

Trp Ala Val Cys His Leu
1 5

<210> SEQ ID NO 57
<211> LENGTH: 5
<212> TYPE: PRT
<213> ORGANISM: Artificial
<220> FEATURE:
<223> OTHER INFORMATION: metallopeptide derived from bombesin analog

<400> SEQUENCE: 57

Ala Val Cys His Leu
1 5

<210> SEQ ID NO 58
<211> LENGTH: 6
<212> TYPE: PRT
<213> ORGANISM: Artificial
<220> FEATURE:
<223> OTHER INFORMATION: metallopeptide derived from bombesin analog

<400> SEQUENCE: 58

Gln Trp Ala Val Cys His
1 5

<210> SEQ ID NO 59
<211> LENGTH: 5
<212> TYPE: PRT
<213> ORGANISM: Artificial
<220> FEATURE:
<223> OTHER INFORMATION: metallopeptide derived from bombesin analog

<400> SEQUENCE: 59

Trp Ala Val Cys His
1 5

<210> SEQ ID NO 60
<211> LENGTH: 4
<212> TYPE: PRT
<213> ORGANISM: Artificial
<220> FEATURE:
<223> OTHER INFORMATION: metallopeptide derived from bombesin analog

<400> SEQUENCE: 60

-continued

Ala Val Cys His
1

<210> SEQ ID NO 61
<211> LENGTH: 5
<212> TYPE: PRT
<213> ORGANISM: Artificial
<220> FEATURE:
<223> OTHER INFORMATION: metallopeptide derived from bombesin analog

<400> SEQUENCE: 61

Gln Trp Ala Val Cys
1 5

<210> SEQ ID NO 62
<211> LENGTH: 4
<212> TYPE: PRT
<213> ORGANISM: Artificial
<220> FEATURE:
<223> OTHER INFORMATION: metallopeptide derived from bombesin analog

<400> SEQUENCE: 62

Trp Ala Val Cys
1

<210> SEQ ID NO 63
<211> LENGTH: 4
<212> TYPE: PRT
<213> ORGANISM: Artificial
<220> FEATURE:
<223> OTHER INFORMATION: Alpha-MSH message segment

<400> SEQUENCE: 63

His Phe Arg Trp
1

<210> SEQ ID NO 64
<211> LENGTH: 4
<212> TYPE: PRT
<213> ORGANISM: Artificial
<220> FEATURE:
<223> OTHER INFORMATION: Bombesin critical peptide segment

<400> SEQUENCE: 64

Gln Trp Ala Val
1

<210> SEQ ID NO 65
<211> LENGTH: 11
<212> TYPE: PRT
<213> ORGANISM: Artificial
<220> FEATURE:
<223> OTHER INFORMATION: metallopeptide derived from melanocortin
receptor binding compound
<220> FEATURE:
<221> NAME/KEY: MISC_FEATURE
<222> LOCATION: (3)..(3)
<223> OTHER INFORMATION: Norleucine

<400> SEQUENCE: 65

Tyr Val Xaa Gly His Cys Arg Trp Asx Arg Phe
1 5 10